(12) United States Patent
Degbia et al.

(10) Patent No.: US 10,403,445 B2
(45) Date of Patent: Sep. 3, 2019

(54) SYNTHONS FOR DEVELOPING ORGANIC SEMICONDUCTORS

(71) Applicant: UNIVERSITÉ DE TOURS, Tours (FR)

(72) Inventors: Martial Degbia, Tours (FR); Bruno Schmaltz, Monts (FR); François Tran-Van, Fondettes (FR)

(73) Assignee: UNIVERSITÉ DE TOURS, Tours (FR)

( * ) Notice: Subject to any disclaimer, the term of this patent is extended or adjusted under 35 U.S.C. 154(b) by 0 days.

(21) Appl. No.: 15/329,731

(22) PCT Filed: Jul. 28, 2015

(86) PCT No.: PCT/EP2015/067232
§ 371 (c)(1),
(2) Date: Jan. 27, 2017

(87) PCT Pub. No.: WO2016/016221
PCT Pub. Date: Feb. 4, 2016

(65) Prior Publication Data
US 2017/0213652 A1   Jul. 27, 2017

(30) Foreign Application Priority Data

Jul. 28, 2014   (FR) ..................... 14 57308

(51) Int. Cl.
*C07D 209/88* (2006.01)
*H01G 9/20* (2006.01)
*H01L 51/00* (2006.01)

(52) U.S. Cl.
CPC ......... *H01G 9/2018* (2013.01); *C07D 209/88* (2013.01); *H01G 9/2027* (2013.01); *H01G 9/2059* (2013.01); *H01L 51/006* (2013.01); *H01L 51/0061* (2013.01); *H01L 51/0052* (2013.01); *H01L 51/0072* (2013.01)

(58) Field of Classification Search
CPC .................................................. C07D 209/88
See application file for complete search history.

(56) References Cited

U.S. PATENT DOCUMENTS

| 6,660,410 | B2 | 12/2003 | Hosokawa |
| 7,597,967 | B2 | 10/2009 | Kondokova et al. |
| 8,198,801 | B2 | 6/2012 | Kim et al. |
| 8,974,923 | B2 | 3/2015 | Muta et al. |
| 9,153,788 | B2 | 10/2015 | Adachi et al. |
| 9,543,530 | B2 | 1/2017 | Kim et al. |
| 2006/0051690 | A1 | 3/2006 | Matoliukstyte et al. |
| 2006/0182995 | A1 | 8/2006 | Chang et al. |

FOREIGN PATENT DOCUMENTS

| JP | 2002047271 A | 2/2002 |
| JP | 2004-171808 A | 6/2004 |
| JP | 2005-154412 A | 6/2005 |
| JP | 2005-154421 A | 6/2005 |
| JP | 2006-056841 A | 3/2006 |
| JP | 2006-352069 A | 12/2006 |
| JP | 2011-001475 A | 1/2011 |
| JP | 2014-506262 A | 3/2014 |
| WO | 2005040117 A1 | 5/2005 |
| WO | 2013/012298 A1 | 1/2013 |

OTHER PUBLICATIONS

Oyama, et al. Accession No. 157:300557, retrieved from STN; Aug. 2, 2012.*
No new references cited by the Examiner.*
Buu-Hoï et al. "Potential Nitrogen-Heterocycle Carcinogens: XI. Substitution Reactions of N-Alkylcarbazoles" Journal of Organic Chemistry (1951), 16(8), pp. 1198-1205.
Degbia et al. "Carbazole Based Hole Transporting Materials for Solid State Dye Sensitizer Solar Cells: Role of the Methoxy Groups" Polymer International (2014), 63(8), pp. 1387-1393.
Estrada et al. "Synthesis and Photophysics of Dibenz-[a,c]phenazine Derivatives" Organic Letters (2011), 13(13), pp. 3304-3307.
Haddach et al. "An Efficient Method for the N-debenzylation of Aromatic Heterocycles" Tetrahedron Letters (2002), 43(3), pp. 339-402.
Kundu et al. "High-Tg Carbazole Derivatives as Blue-Emitting Hole-Transporting Materials for Electroluminescent Devices" Advanced Functional Materials (2003), 13(6), pp. 445-452.
Leijtens et al. "Hole Transport Materials with Low Glass Transition Temperatures and High Solubility for Application in Solid-State Dye-Sensitized Solar Cell" ASC NANO (2012), 6(2), pp. 1455-1462.
Li et al. "Theoretical Studies of the Structural, Electronic and Optical Properties of Carbazole-Based Compounds" Journal of Physical Organic Chemistry (2012), 25(4), pp. 334-342.
Puckyte et al. "Carbazole-Based Molecular Glasses for Efficient Solid-State Dye-Sensitized Solar Cells" Journal of Power Sources (2013), vol. 233, pp. 86-92.
Shen et al. "Ambipolar Conductive 2,7-Carbazole Derivatives for Electroluminescent Devices" Advanced Functional Materials (2007), vol. 17, pp. 983-995.
Thomas et al. "Light-Emitting Carbazole Derivatives: Potential Electroluminescent Materials" Journal of the American Chemical Society (2001), 123(38), pp. 9404-9411.
Tomkeviciene et al. "Dimethyldiphenylamino-Substituted Carbazoles as Electronically Active Molecular Materials" Dyes and Pigments (2013), 96(2), pp. 574-580.
Tomkeviciene et al. "Diphenylamino-Substituted Derivatives of 9-Phenylcarbazole as Glass-Forming Hole-Transporting Materials for Solid State Dye Sensitized Solar Cells" Synthetic Metals (2012), 162(23), pp. 1997-2004.
Tucker et al. "Iodination in the Carbazole Series" Journal of the Chemical Society (1926), vol. 129, pp. 546-553.

(Continued)

Primary Examiner — Shawquia Jackson
(74) Attorney, Agent, or Firm — Greer, Burns & Crain, Ltd.

(57) ABSTRACT

A process for the synthesis of π-conjugated materials including a step of utilizing a synthon having a carbazole or fluorene nucleus.

8 Claims, 1 Drawing Sheet

(56) References Cited

OTHER PUBLICATIONS

Yamamoto et al. "Palladium-Catalyzed Synthesis of Triarylamines from Aryl Halides and Diarylamines" Tetrahedron Letters (1998), 39(16), pp. 2367-2370.
Zhang et al. "Novel Hole-Transporting Materials Based on 1,4-Bis(Carbazolyl)Benzene for Organic Light-Emitting Devices" Journal of Materials Chemistry (2000), 14(5), pp. 895-900.
French Search Report from French Patent Application No. 1457308, dated Feb. 6, 2015.
International Search Report from International Patent Application No. PCT/EP2015/067232, dated Oct. 13, 2015.
Japanese Office Action from corresponding Japanese Patent Application No. 2017-505229, dated Apr. 23, 2019.
Baycan Koyuncu et al. "A New Multi-Electrochromic 2,7 Linked Polycarbazole Derivative: Effect of the Nitro Subunit" Organic Electronics (2011), 12(10), pp. 1701-1710.
Lee et al. "New Organic Dye Based on a 3,6-Disubstituted Carbazole Donor for Efficient Dye-Sensitized Solar Cells" Chemistry, An Asian Journal (2012), 7(2), pp. 343-350.
Matoliukstyte et al. "Condensed Aromatic Amines as Electroactive Materials for Optoelectronic Applications" Molecular Crystals and Liquid Crystals (2007), 468(1), pp. 95/[447]-105/[457].
Mohamad et al. "Aryl Amine Substituted Low Energy Gap Carbazole Polymers: Preparation and Photovoltaic Properties" Journal of Materials Chemistry (2010), 20(33), pp. 6990-6997.
Pan et al. "Novel Fluorescent Carbazolyl—Pyridinyl Alternating Copolymers: Synthesis, Characterization, and Properties" Macromolecules (2005), 38(18), pp. 7629-7635.

\* cited by examiner

SYNTHONS FOR DEVELOPING ORGANIC SEMICONDUCTORS

BACKROUND

The present invention relates to novel synthons, a process for their preparation and their use in the development of various materials, in particular organic semiconductors and dyes.

Solar cells with photosensitive pigment (dye-sensitized solar cells or DSSCs) are a promising photovoltaic technology for the production of low-cost renewable energy. These cells are constituted by a nanocrystalline oxide with a wide energy gap, for example $TiO_2$ deposited as a transparent conductive oxide onto a glass support. Molecular sensitizers, linked via anchoring groups to a wide gap oxide, under exposure to the sun inject electrons into the conduction band of the semiconductor. Usually, a liquid electrolyte comprising a redox system ensures the regeneration of the photo-excited dye.

Today, DSSCs based on liquid electrolytes achieve conversion efficiencies of greater than 12%. However, they can present problems of leakage and corrosion of the electrodes.

A strategy that was developed a few years ago consists of the manufacture of "solid state" DSSCs (ssDSSCs) obtained by replacing the liquid electrolyte with a p-type organic semiconductor or a polymer matrix combined with a redox couple. To this end, various pi-conjugated compounds such as derivatives of triphenylamine, carbazole or conjugated polymers such as poly(3,4-ethylenedioxythiophene) (PEDOT) or poly-3-hexylthiophene (P3HT) have been proposed. Currently, one of the most studied materials is 2,2,7,7-tetrakis-(N,N-di-p-methoxyphenylamine)-9,9-spirobifluorene or spiro-OMeTAD which has become the molecule of reference for an organic semiconductor that is a hole transporter. The results obtained with this type of molecular glass exceed those obtained with liquid cells, since the use of perovskite-type sensitizers, which have made it possible to achieve conversion efficiencies of greater than 15%.

Recently, the inventors have carried out the synthesis of new hole transport materials having an organic nature based on carbazole disubstituted in positions 3 and 6 that can be used for the manufacture of molecular glasses (Martial Degbia et al., Carbazole-based molecular glasses for 3.44% efficient solid-state dye-sensitized solar cells *Journal of Power Sources*, 233 (2013) 86-92); among the compounds described, 3,6-di(4,4-dimethoxydiphenylaminyl)-9-phenyl-carbazole was found to be very promising, since it gives results that are almost as high as for the Spiro-OMeTAD conventionally used with conversion efficiencies of the order of 3.44% under conditions of production of PV devices that are not optimized.

Although these all-solid-state dye devices can be easily produced, thus making it possible to overcome the problems of corrosion of the electrolyte, leakage and temperature limitation, the processes allowing access to these molecules, in particular the molecule of reference (spiro-OMeTAD) still remain very expensive.

Therefore it is necessary to find novel synthons making it possible to easily prepare a range of high-performance molecular glasses at a low cost, from modulable chemical structures that have a common nucleus suitable for the production of all-solid-state DSSCs having a high solar power conversion efficiency.

SUMMARY

Now, the inventors have discovered that starting from specific synthons, in particular synthons based on carbazole or fluorene, that are easily modifiable chemically, it is possible to prepare a broad range of hole-transporting amorphous molecules, having good mobility, energy levels suitable for regeneration of the photooxidized dye, and having optical and semi-conductive properties suitable for use in DSSCs. The benefit of these synthons is the possibility of developing numerous π-conjugated organic materials, in particular as a result of the reactivity of position 9 on the carbazole or fluorene ring. The synthesis of these π-conjugated materials, even if they have complex structures, can be carried out in a single step starting from said synthons and a well-chosen connecting centre.

These π-conjugated materials have applications in optoelectronics, in particular for charge transport and/or photon absorption. By way of example, OLEDs, organic transistors and organic and hybrid photovoltaic cells may be mentioned.

Thus the purpose of the invention is to provide a method for the preparation of π-conjugated materials starting from novel synthons.

A further purpose of the invention is to provide novel synthons and their manufacturing process.

Thus the present invention relates to a process for the synthesis of π-conjugated materials comprising a step of utilizing a synthon of formula (I)

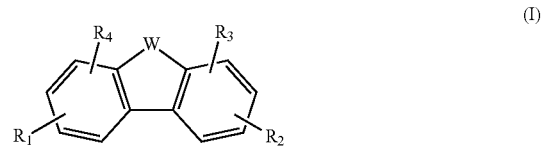

(I)

in which
W represents either a —CHR$_5$— group, or an —N(H)— group,
R$_1$ and R$_2$, identical or different, are respectively in position 3 and 6 or in position 2 and 7 of the ring and are selected independently of one another from the group comprising
 i. hydrogen,
 ii. the mono- or polycyclic aromatic groups, said groups being able to be substituted by at least one straight or branched $C_1$-$C_{12}$ alkyl group, in particular a methyl group, or by a straight or branched $C_1$-$C_{12}$ alkoxy group, in particular a methoxy,
 iii. the

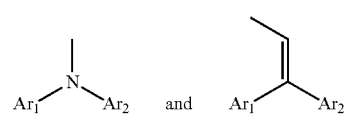

groups in which Ar$_1$ and Ar$_2$, identical or different, each represent independently of one another an aryl group, optionally substituted by one or more substituents, identical or different, selected from:
 a. the hydrogen atom,
 b. the straight or branched $C_1$-$C_{12}$ alkyl groups, said alkyl groups being able to be saturated or unsaturated and being able to comprise one or more heteroatoms selected from O and S,
 c. the straight or branched $C_1$-$C_{12}$ alkoxy groups, said alkoxy groups being able to be saturated or unsaturated and being able to comprise one or more heteroatoms selected from O and S, d. the oligoethers and
e. the oligothioethers, provided that $R_1$ and $R_2$ are not simultaneously a hydrogen atom, $R_3$ and $R_4$, identical or different, occupy the positions left free by $R_1$ and $R_2$ and are selected from:
a. hydrogen,
b. the halogens
c. the nitro group,
d. the sulphonate group,
e. the amine groups,
f. the carbonyl groups,
g. the mono- or polycyclic aromatic groups
h. the straight or branched $C_1$-$C_{12}$ alkyl groups, said alkyl groups being able to be saturated or unsaturated and being able to comprise one or more heteroatoms selected from O and S,
i. the straight or branched $C_1$-$C_{12}$ alkoxy groups, said alkoxy groups being able to be saturated or unsaturated and being able to comprise one or more heteroatoms selected from O and S,
j. the oligoethers and
k. the oligothioethers.

$R_5$ is selected from:
a. the straight or branched $C_1$-$C_{12}$ alkyl groups, said alkyl groups being able to be saturated or unsaturated and being able to comprise one or more heteroatoms selected from O and S,
b. the oligoethers and
c. the oligothioethers.

In an advantageous embodiment of the process of the invention, $R_1$ and $R_2$, identical or different, are respectively in position 3 and 6 or in position 2 and 7 of the ring and are selected independently of one another from the group comprising
i. hydrogen,
ii. the mono- or polycyclic aromatic groups, said groups being able to be substituted by at least one straight or branched $C_1$-$C_{12}$ alkyl group, in particular a methyl group, or by a straight or branched $C_1$-$C_{12}$ alkoxy group, in particular a methoxy,
iii. the

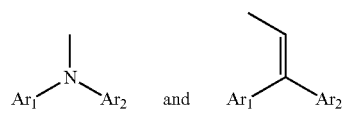

groups in which $Ar_1$ and $Ar_2$, identical or different, each represent independently of one another an aryl group, optionally substituted by one or more substituents, identical or different, selected from:
a. the straight or branched $C_1$-$C_{12}$ alkoxy groups, said alkoxy groups being able to be saturated or unsaturated and being able to comprise one or more heteroatoms selected from O and S,
b. the oligoethers and
c. the oligothioethers, provided that $R_1$ and $R_2$ are not simultaneously a hydrogen atom, When W represents a —$CR_5$— group, then the synthon is a fluorene derivative of formula (Ia)

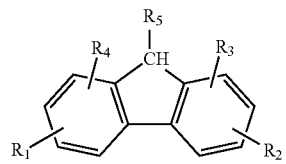

and when W represents an —N(H)— group, then the synthon is a carbazole derivative of formula (Ib)

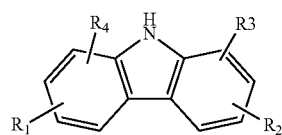

When $R_1$ et $R_2$ are in position 3 and/or 6 or 2 and/or 7 of the carbazole ring, then $R_3$ et $R_4$ are in position 1 and 5 or 4 and 8 of said ring.

Within the meaning of the present invention, the mono- or polycyclic aromatic groups comprise from 6 to 50 carbon atoms. Advantageously, they comprise from 6 to 18 carbon atoms and are mono-, bi- or tricyclic. When the carbocyclic group comprises more than one cyclic nucleus, the cyclic nuclei can be fused in pairs or attached in pairs by a bonds. Two fused nuclei can be ortho-fused or peri-fused. The carbocyclic radical can comprise a saturated part and/or an aromatic part and/or an unsaturated part. By way of example the ($C_6$-$C_{18}$)aryl groups and in particular phenyl, benzyl, tolyl, xylyl, naphthyl, anthryl, phenanthryl, biphenyl, terphenyl, tetrahydronaphthyl, fluorene and carbazole groups may be mentioned. These mono- or polycyclic, and in particular mono-, bi-, or tricyclic radicals can comprise one or more heteroatoms selected from O, S and/or N, preferably 1 to 4 heteroatoms. Preferably, the monocycles or the monocycle constituting the heterocycle has 5 to 12 members, more preferably from 5 to 10 members, for example from 5 to 6 members. By way of example, unsaturated or aromatic mono- or polycyclic heterocycles, pyridine, furan, thiophene, pyrrole, pyrrazole, imidazole, thiazole, isoxazole, isothiazole, pyridazine, pyrimidine, pyrazine, triazines, indolizine, indole, isoindole, benzofuran, benzothiophene, indazole, benzimidazole, benzothiazole, purine, quinoline, isoquinoline, cinnoline, phthalazine, quinazoline, quinoxaline, pteridine, naphthyridines, carbazole, phenothiazine, phenoxazine, acridine, phenazine, oxazole, pyrazole, oxadiazole, triazole, thiadiazole and unsaturated derivatives thereof may be mentioned. Other examples are the unsaturated derivatives of pyrrolidine, dioxolane, imidazolidine, pyrazolidine, piperidine, dioxane, morpholine, dithiane, thiomorpholine, piperazine and trithiane.

According to the invention, by $C_1$-$C_{12}$ alkyl, or straight or branched ($C_1$-$C_{12}$)alkyl group, is meant said alkyl group being able to be saturated or unsaturated and being able to comprise one or more heteroatoms selected from O and S, a linear or branched, saturated or unsaturated chain with 1 to 15 carbon atoms, said carbon atoms being able to be replaced with one or more heteroatoms selected from O and S. By way of example methyl, ethyl, propyl, isopropyl, butyl, isobutyl, sec-butyl, tent-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 2-ethylbutyl, 1-methyl-1-ethylpropyl, heptyl, 1-methylhexyl, 1-propylbutyl, 4,4-dimethylpentyl, octyl, 1-methylheptyl, 2-ethylhexyl, 5,5-dimethylhexyl, nonyl, decyl, 1-methylnonyl, 3,7-dimethyloctyl and 7,7-dimethyloctyl groups may be mentioned.

According to the invention, the straight or branched $C_1$-$C_{12}$ or ($C_1$-$C_{12}$)alkoxy groups represent an alkoxy group comprising from 1 to 12 carbon atoms, said alkoxy groups being able to be saturated or unsaturated and being able to comprise one or more heteroatoms selected from O and S. By way of example the methoxy, ethoxy, propoxy, iso-propoxy, butoxy, isobutoxy, sec-butoxy and tert-butoxy groups may be mentioned.

According to the invention, by oligoethers group is meant oligomers the organic repetition units of which are held together by ether functions (C—O—C). Advantageously, the oligoethers according to the invention comprise two to five ether groups and from 2 to 4 repetition units. By way of example of oligoethers, diethylene glycol, triethylene glycol, tetraethylene glycol, pentaethylene glycol may be mentioned.

According to the invention, by oligoethers group is meant oligomers the organic repetition units of which are held together by thioether functions (C—S—C). Advantageously, the oligothioethers according to the invention comprise two to three thioether groups and from 2 to 4 repetition units. By way of example of oligothioethers, ethanedithiol may be mentioned.

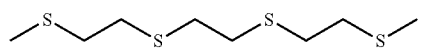

According to the invention, by halogen is meant an atom selected from the group comprising bromine, chlorine, fluorine and iodine.

According to the invention, by nitro group is meant an $NO_2$ group, and by sulphonate group, a —$SO_2$ group.

According to the invention, by amine groups is meant primary (—$NH_2$), secondary or tertiary amines.

According to the invention, by carbonyl groups is meant the =C=O, —CHO, —COR groups, R being a $C_1$-$C_{12}$ alkyl group.

By way of example of particularly advantageous groups for $R_1$ et $R_2$ there may be mentioned:

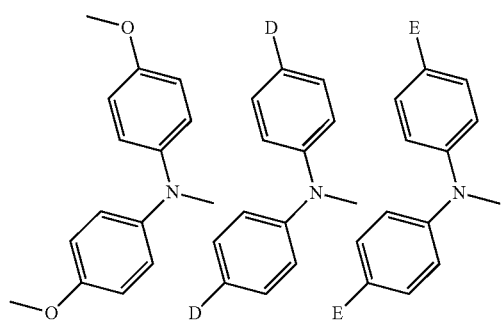

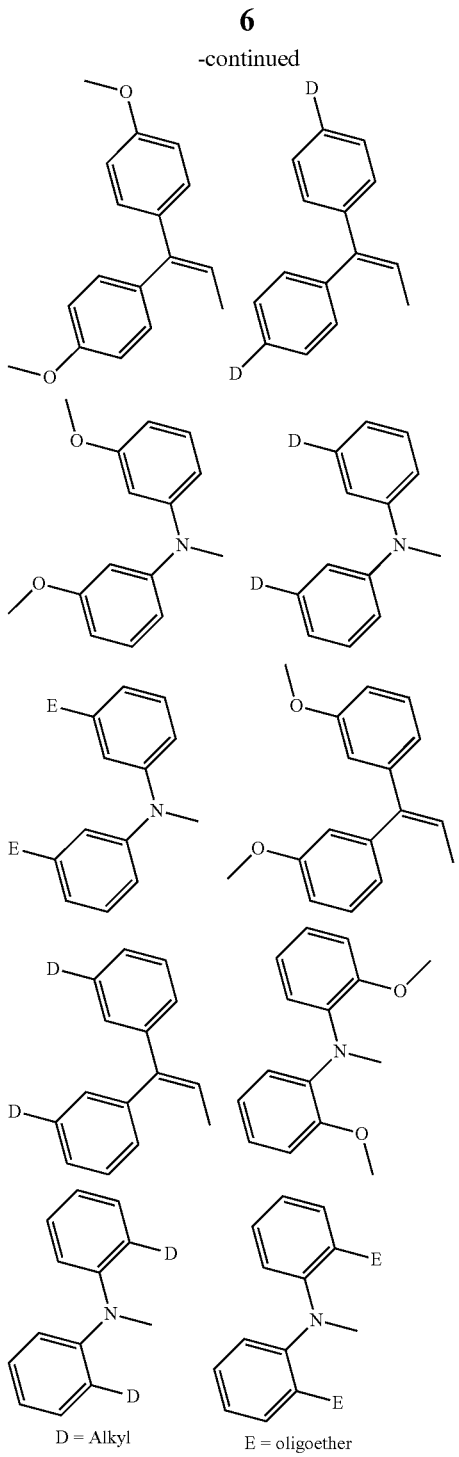

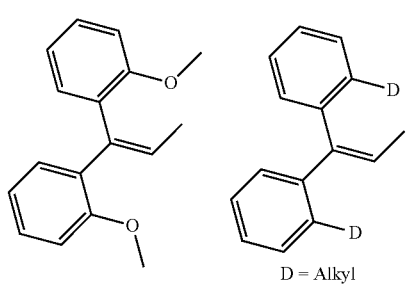

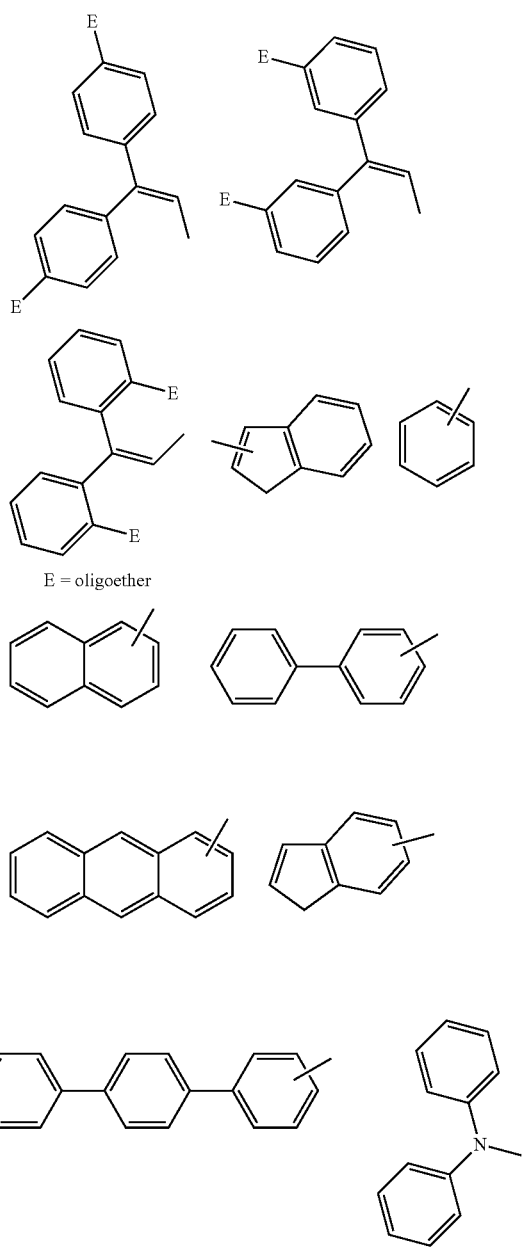

E = oligoether

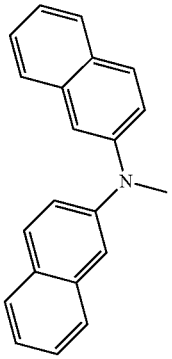 [SMILES: CN(c1ccc2ccccc2c1)c1ccc2ccccc2c1]

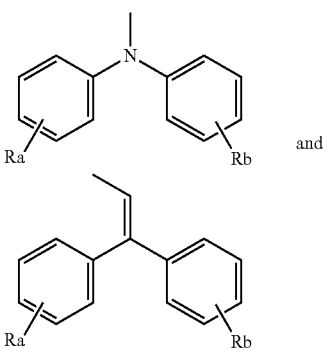

In an advantageous embodiment of the process of the invention, a compound of formula (I) is used, in which $R_1$ and $R_2$ each represent, independently of one another, a group selected from:
i. the phenyl, naphthyl, anthracenyl, indenyl, biphenyl, terphenyl, carbazolyl groups, said groups being able to be substituted by at least one straight or branched $C_1$-$C_{12}$ alkyl group, in particular a methyl group,
ii. the groups in which Ra and Rb, identical or different, each represent, independently of one another:
  a. either a hydrogen atom,
  b. or a straight or branched $C_1$-$C_{12}$ alkyl group, said alkyl group being able to be saturated or unsaturated and being able to comprise one or more heteroatoms selected from O and S,
  c. or a straight or branched $C_1$-$C_{12}$ alkoxy group, said alkoxy group being able to be saturated or unsaturated and being able to comprise one or more heteroatoms selected from O and S, in particular a methoxy group,
  d. or an oligoether,
  e. or an oligothioether.

In a more advantageous embodiment of the process of the invention, a compound of formula (I) is used, in which $R_1$ and $R_2$ each represent, independently of one another, a group selected from the

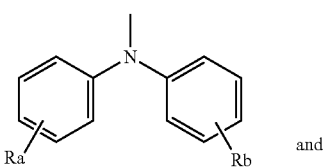

and

-continued

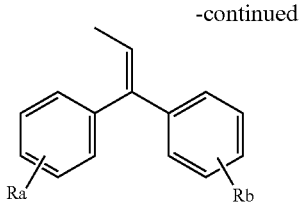

groups in which Ra and Rb, identical or different, each represent, independently of one another:
a. either a straight or branched $C_1$-$C_{12}$ alkoxy group, said alkoxy group being able to be saturated or unsaturated and being able to comprise one or more heteroatoms selected from O and S, in particular a methoxy group,
b. or an oligoether,
c. or an oligothioether.

In an even more advantageous embodiment of the process of the invention, compounds of formula (I) are utilized, in which $R_3$ and $R_4$ each represent a hydrogen atom; these compounds therefore correspond to formula (I')

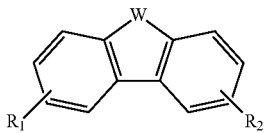

(I')

in which $R_1$ and $R_2$ are as previously defined.

The process of the invention makes it possible to prepare a wide range of π-conjugated materials having different structure and properties, in particular compounds of formula (Ib')

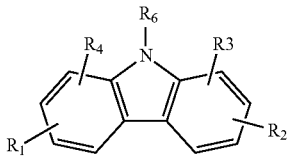

(Ib')

in which
$R_1$ and identical or different, are respectively in position 3 and 6 or in position 2 and 7 of the ring and are selected independently of one another from the group comprising
i. hydrogen,
ii. the aryl groups, said aryl groups being able to be substituted by at least one straight or branched $C_1$-$C_5$ alkyl group, in particular a methyl group,
iii. the

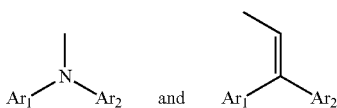

groups in which $Ar_1$ and $Ar_2$, identical or different, each represent independently of one another an aryl group, optionally substituted by one or more substituents, identical or different, selected from:

a. the hydrogen atom,
b. the straight or branched $C_1$-$C_{12}$ alkyl groups, said alkyl groups being able to be saturated or unsaturated and being able to comprise one or more heteroatoms selected from O and S,
c. the straight or branched $C_1$-$C_{12}$ alkoxy groups, said alkoxy groups being able to be saturated or unsaturated and being able to comprise one or more heteroatoms selected from O and S,
d. the oligoethers and
e. the oligothioethers,
provided that $R_1$ and $R_2$ are not simultaneously a hydrogen atom,
$R_3$ and $R_4$, identical or different, occupy the positions left free by $R_1$ and $R_2$ and are selected from:
a. hydrogen,
b. the halogens
c. the nitro group,
d. the sulphonate group,
e. the amine groups,
f. the carbonyl groups,
g. the mono- or polycyclic aromatic groups
h. the straight or branched $C_1$-$C_{12}$ alkyl groups, said alkyl groups being able to be saturated or unsaturated and being able to comprise one or more heteroatoms selected from O and S,
i. the straight or branched $C_1$-$C_{12}$ alkoxy groups, said alkoxy groups being able to be saturated or unsaturated and being able to comprise one or more heteroatoms selected from O and S,
j. the oligoethers and
k. the oligothioethers.
and
$R_6$ represents either a straight or branched $C_1$-$C_{12}$ alkyl group, or a $C_6$-$C_{18}$ aryl group, in particular a benzene or methoxybenzene (anisole) group, or an amine protecting group, in particular a benzyl group, optionally substituted by a $C_1$-$C_5$ alkoxy group, or a $C_6$-$C_{18}$ aryl group substituted by a halogen, in particular fluorine or substituted by a straight or branched fluorinated $C_1$-$C_{12}$ alkyl group, in particular trifluoromethyl (CF3), or a bi-, tri or tetracyclic group comprising from 10 to 18 carbon atoms, such as for example a naphthyl, tetrahydronaphthyl, anthracenyl or pyrenyl group.

In an advantageous embodiment, the compounds prepared according to the process of the invention correspond to formula (Ib') in which
$R_1$ and $R_2$, identical or different, are respectively in position 3 and 6 or in position 2 and 7 of the ring and are selected independently of one another from the group comprising
i. hydrogen,
ii. the aryl groups, said aryl groups being able to be substituted by at least one straight or branched $C_1$-$C_5$ alkyl group, in particular a methyl group,
iii. the

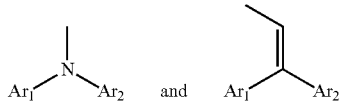

groups in which $Ar_1$ and $Ar_2$, identical or different, each represent independently of one another an aryl group, optionally substituted by one or more substituents, identical or different, selected from:

a. the straight or branched $C_1$-$C_{12}$ alkoxy groups, said alkoxy groups being able to be saturated or unsaturated and being able to comprise one or more heteroatoms selected from O and S,
b. the oligoethers and
c. the oligothioethers,
provided that $R_1$ and $R_2$ are not simultaneously a hydrogen atom,
$R_3$ and $R_4$, identical or different, occupy the positions left free by $R_1$ and $R_2$ and are selected from:
a. hydrogen,
b. the halogens
c. the nitro group,
d. the sulphonate group,
e. the amine groups,
f. the carbonyl groups,
g. the mono- or polycyclic aromatic groups
h. the straight or branched $C_1$-$C_{12}$ alkyl groups, said alkyl groups being able to be saturated or unsaturated and being able to comprise one or more heteroatoms selected from O and S,
i. the straight or branched $C_1$-$C_{12}$ alkoxy groups, said alkoxy groups being able to be saturated or unsaturated and being able to comprise one or more heteroatoms selected from O and S,
j. the oligoethers and
k. the oligothioethers.
and
$R_6$ represents either a straight or branched $C_1$-$C_{12}$ alkyl group, or a $C_6$-$C_{18}$ aryl group, in particular a benzene or methoxybenzene (anisole) group, or an amine protecting group, in particular a benzyl group, optionally substituted by a $C_1$-$C_5$ alkoxy group, or a $C_6$-$C_{18}$ aryl group substituted by a halogen, in particular fluorine or substituted by a straight or branched fluorinated $C_1$-$C_{12}$ alkyl group, in particular trifluoromethyl (CF3), or a bi-, tri or tetracyclic group comprising from 10 to 18 carbon atoms, such as for example a naphthyl, tetrahydronaphthyl, anthracenyl or pyrenyl group.

The process of the invention also makes it possible to prepare π-conjugated materials corresponding to formula (1a) or (1b)

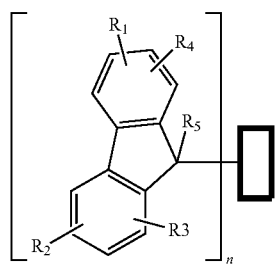

(1a)

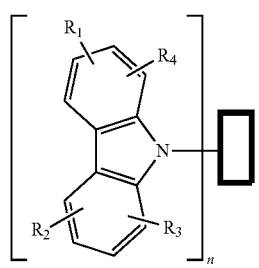

(1b)

in which

represents a polyfunctional central unit. By polyfunctional unit is meant a unit bearing functions allowing grafting in position 9 of the carbazole nucleus or of the fluorene nucleus. By way of example of functions allowing grafting; iodine, bromine, chlorine atoms, tosylates, mesylates, etc. may be mentioned. By way of example of polyfunctional central units, —$C_6H_4$—, biphenylene, terphenyl, fluorenyl, carbazolyl, oligooxyethylene derivative may be noted, these polyfunctional central units being able to be substituted or not by one or more linear or branched $C_1$-$C_{12}$ alkyls.

n is an integer equal to or greater than 2, advantageously comprised between 2 and 6, $R_1$ and $R_2$, identical or different, are respectively in position 3 and 6 or in position 2 and 7 of the ring and are selected independently of one another from the group comprising
i. hydrogen,
ii. the aryl groups, said aryl groups being able to be substituted by at least one straight or branched $C_1$-$C_5$ alkyl group, in particular a methyl group,
iii. the

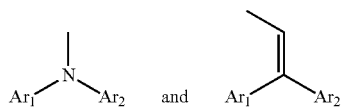

groups in which $Ar_1$ and $Ar_2$, identical or different, each represent independently of one another an aryl group, optionally substituted by one or more substituents, identical or different, selected from:
a. the hydrogen atom,
b. the straight or branched $C_1$-$C_{12}$ alkyl groups, said alkyl groups being able to be saturated or unsaturated and being able to comprise one or more heteroatoms selected from O and S,
c. the straight or branched $C_1$-$C_{12}$ alkoxy groups, said alkoxy groups being able to be saturated or unsaturated and being able to comprise one or more heteroatoms selected from O and S,
d. the oligoethers and
e. the oligothioethers,
provided that $R_1$ and $R_2$ are not simultaneously a hydrogen atom,
$R_3$ and $R_4$, identical or different, occupy the positions left free by $R_1$ and $R_2$ and are selected from:
a. hydrogen,
b. the halogens
c. the nitro group,
d. the sulphonate group,
e. the amine groups,
f. the carbonyl groups,
g. the mono- or polycyclic aromatic groups
h. the straight or branched $C_1$-$C_{12}$ alkyl groups, said alkyl groups being able to be saturated or unsaturated and being able to comprise one or more heteroatoms selected from O and S, i. the straight or branched $C_1$-$C_{12}$ alkoxy groups, said alkoxy groups being able to be saturated or unsaturated and being able to comprise one or more heteroatoms selected from O and S, j. the oligoethers and k. the oligothioethers, $R_5$ represents:

a) either a straight or branched $C_1$-$C_{12}$ alkyl group, said alkyl groups being able to be saturated or unsaturated and being able to comprise one or more heteroatoms selected from O and S, b) or the oligoethers and c) optionally the oligothioethers.

By way of example, compounds of formula (1a1) and (1b1) may be mentioned.

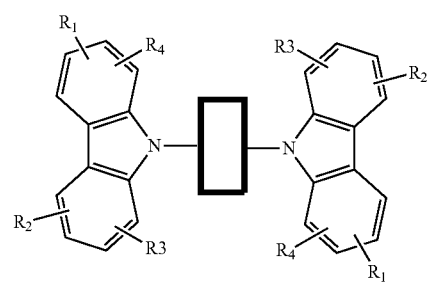
(1b1)

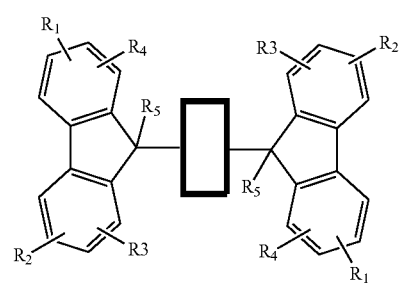
(1a1)

corresponding to compounds of formula (1a) and (1b) for which n=2.

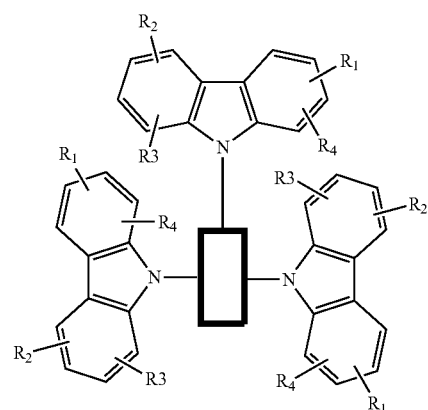
(1b2)

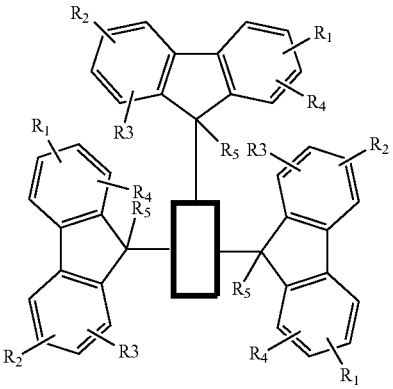
(1a2)

corresponding to compounds of formula (1a) and (1b) for which n=3

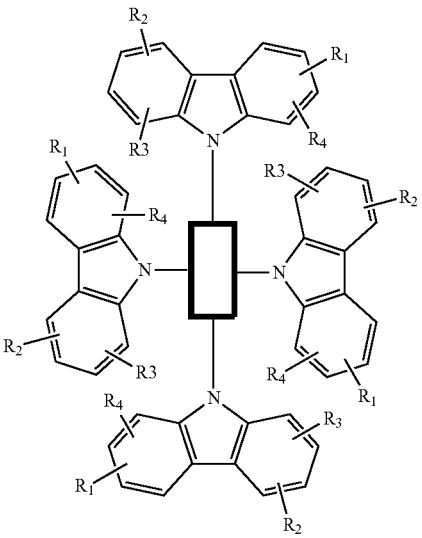
(1b3)

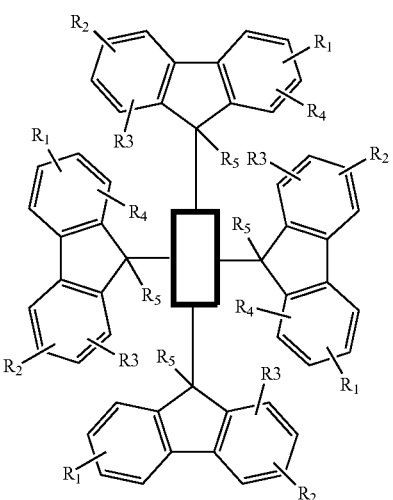
(1a3)

corresponding to compounds of formula (1a) and (1b) for which n=4.

The benefit of the different synthons utilized in the process according to the invention is the possibility of developing numerous π-conjugated organic materials, in particular as a result of the reactivity of position 9 on the carbazole ring or position 9 on the fluorene ring. The π-conjugated organic materials derived from said synthons can be polyfunctional, i.e. they have a centre connected to several synthons. Thus the process according to the invention gives a wide possibility for the synthesis of new π-conjugated organic materials. In addition, the synthesis of these π-conjugated materials is facilitated by the use of the synthon since it is possible to access certain π-conjugated materials having complex structures in a single step starting from this synthon.

These π-conjugated materials have applications in optoelectronics, in particular for charge transport and/or photon absorption. By way of example, OLEDs, organic transistors, organic, hybrid and perovskite photovoltaic cells may be mentioned.

The compounds of formula (Ia), (Ib) et (Ib')

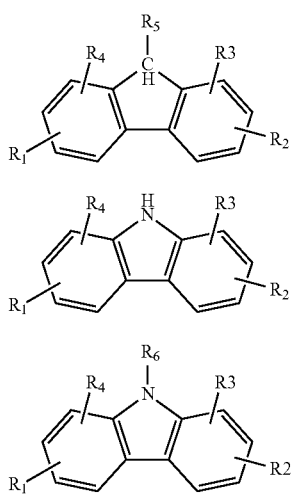

in which $R_1$ and $R_2$, identical or different, are respectively in position 3 and 6 or in position 2 and 7 of the ring and are selected independently of one another from the group comprising
  i. hydrogen,
  ii. the halogens
  iii. the aryl groups, said aryl groups being able to be substituted by at least one straight or branched $C_1$-$C_5$ alkyl group, in particular a methyl group,
  iv. the

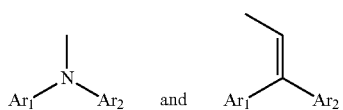

groups in which $Ar_1$ and $Ar_2$, identical or different, each represent independently of one another an aryl group, optionally substituted by one or more substituents, identical or different, selected from:

a. the hydrogen atom,
  b. the straight or branched $C_1$-$C_{12}$ alkyl groups, said alkyl groups being able to be saturated or unsaturated and being able to comprise one or more heteroatoms selected from O and S,
  c. the straight or branched $C_1$-$C_{12}$ alkoxy groups, said alkoxy groups being able to be saturated or unsaturated and being able to comprise one or more heteroatoms selected from O and S,
  d. the oligoethers and
  e. the oligothioethers,
  provided that $R_1$ and $R_2$ are not simultaneously a hydrogen atom, $R_3$ and $R_4$, identical or different, occupy the positions left free by $R_1$ and $R_2$ and are selected from:
  a. hydrogen,
  b. the halogens
  c. the nitro group,
  d. the sulphonate group,
  e. the amine groups,
  f. the carbonyl groups,
  g. the mono- or polycyclic aromatic groups
  h. the straight or branched $C_1$-$C_{12}$ alkyl groups, said alkyl groups being able to be saturated or unsaturated and being able to comprise one or more heteroatoms selected from O and S,
  i. the straight or branched $C_1$-$C_{12}$ alkoxy groups, said alkoxy groups being able to be saturated or unsaturated and being able to comprise one or more heteroatoms selected from O and S,
  j. the oligoethers and
  k. the oligothioethers, $R_5$ is selected from:
  a. the straight or branched $C_1$-$C_{12}$ alkyl groups, said alkyl groups being able to be saturated or unsaturated and being able to comprise one or more heteroatoms selected from O and S,
  b. the oligoethers,
  c. the oligothioethers, $R_6$ represents either a straight or branched $C_1$-$C_{12}$ alkyl group, or a $C_6$-$C_{18}$ aryl group, in particular a benzene or methoxybenzene (anisole) group, or an amine protecting group, in particular a benzyl group, optionally substituted by a $C_1$-$C_5$ alkoxy group, or a $C_6$-$C_{18}$ aryl group substituted by a halogen, in particular fluorine or substituted by a straight or branched fluorinated $C_1$-$C_{12}$ alkyl group, in particular trifluoromethyl (CF3), or a bi-, tri or tetracyclic group comprising from 10 to 18 carbon atoms, such as for example a naphthyl, tetrahydronaphthyl, anthracenyl or pyrenyl group are novel and form part of the invention.

There may be mentioned in particular the compound of the following formula:

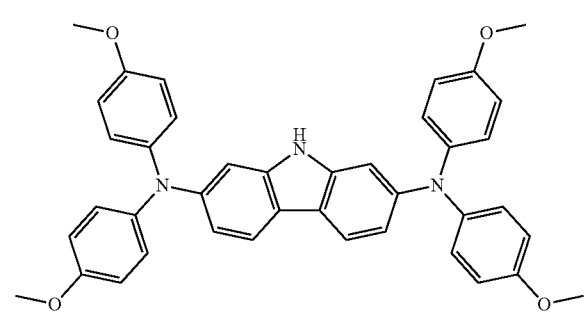

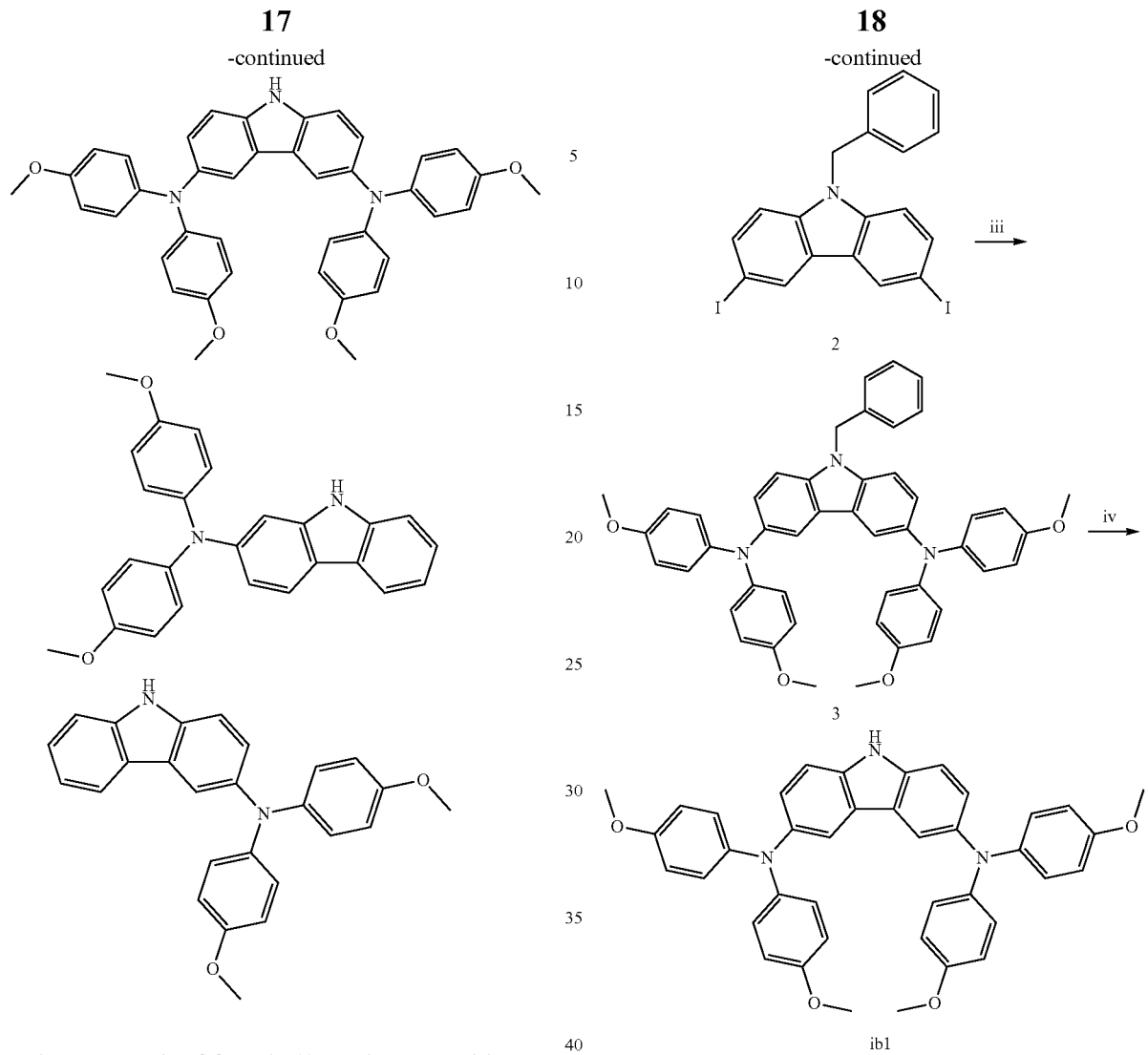

The compounds of formula (I) can be prepared by any technique known to a person skilled in the art, starting from compounds that are commercially available or that can be prepared according to techniques known to a person skilled in the art or described in the literature.

Thus the process illustrated in the following Diagram 1 may be used:

Diagram 1

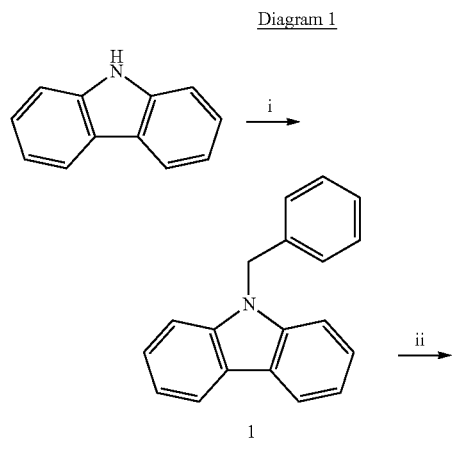

The first step (ii) is the iodation of positions 3 and 6 of the carbazole in acetic acid at 85° C. in the presence of potassium iodide and potassium iodate as described by Tucker, S. H. *J. Chem, Soc.* 1926, 129, 546. This is followed by a second step (i) which consists of protecting the amine in position 9 of the diiodocarbazole with a benzyl group in the presence of sodium hydride in anhydrous tetrahydrofuran (THF) at ambient temperature (Estrada, L. A.; Neckers, D. C. *Organic Letters* 2011, 13, 3304). In a third step, a C—N coupling makes it possible to fix the bis(4-methoxyphenyl)amine group on positions 3 and 6 of the carbazole unit; this step is carried out in toluene at 110° C. in the presence of a palladium catalyst, tri-tert-butylphosphine and sodium butyloxate (Yamamoto, T.; Nishiyama, M.; Koie, Y. *Tetrahedron Letters* 1998, 39, 2367). The last step is a deprotection reaction making it possible to remove the benzyl group from position 9 of the carbazole nucleus so as to render the amine function available for a subsequent use; it is carried out in THF and dimethyl sulphoxyde (DMSO) in the presence of potassium tert-butylate and oxygen (Haddach, A. A.; Kelleman, A.; Deaton-Rewolinski, M. V. *Tetrahedron letters* 2002, 43, 399).

The compounds of formula (I) as defined previously can also be prepared by a process comprising:
 a) a step of protecting W when N represents an —N(H)— group in the compound of formula (II)

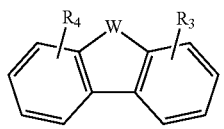
(II)

and
R$_3$ and R$_4$, identical or different, are selected from:
i. hydrogen,
ii. the halogens
iii. the nitro group,
iv. the sulphonate group,
v. the amine groups,
vi. the carbonyl groups,
vii. the mono- or polycyclic aromatic groups,
viii. the straight or branched C$_1$-C$_{12}$ alkyl groups, said alkyl groups being able to be saturated or unsaturated and being able to comprise one or more heteroatoms selected from O and S,
ix. the straight or branched C$_1$-C$_{12}$ alkoxy groups, said alkoxy groups being able to be saturated or unsaturated and being able to comprise one or more heteroatoms selected from O and S,
x. the oligoethers and
xi. the oligothioethers,
provided that if R$_3$ is in position 2 then R$_4$ is not in position 7 and if R$_3$ is in position 3 then R$_4$ is not in position 6,
to give a compound of formula (III)

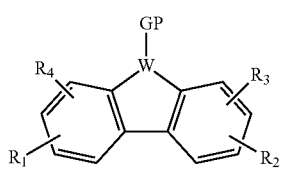
(III)

in which GP is an amine protecting group and in which R$_1$ et R$_2$ represent hydrogens.
b) treating the compound of formula (II) in which W represents a —CHR$_6$— group or a compound of formula (III) with a halogenated derivative, to give a compound of formula (IVa) or (IVb)

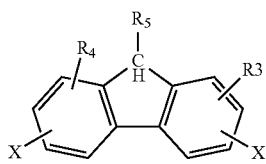
(IVa)

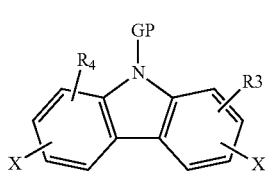
(IVb)

in which
R$_3$ and R$_4$ are as defined in claim 1 and
X, in position 2 and 7 of the fluorene or 3 and 6 of the carbazole represents a halogen atom, in particular an iodine or bromine atom,
c) a coupling reaction of said compound of formula (IVb) or (IVa) to give a compound of formula (Vb) or (Ia)

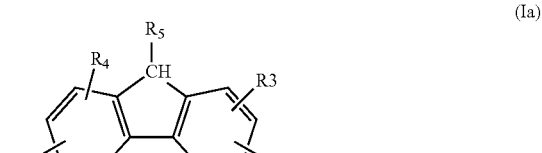
(Ia)

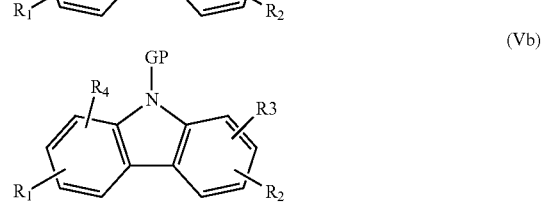
(Vb)

in which R$_1$, R$_2$, R$_3$ and R$_4$ are as previously defined and
d) if necessary, deprotecting the compound of formula (Vb) to give a compound of formula (Ib).

In an advantageous embodiment, the amine protecting group GP is selected from: a benzyl group, optionally substituted by a C$_1$-C$_5$ alkoxy group, the acetyl groups, tert-butyloxycarbonyle (Boc) and carbamate.

The compounds of formula (Ib') in which R$_5$ represents a polycyclic group, in particular a bi-, tri- or tetracyclic group comprising from 10 to 18 carbon atoms, such as for example a naphthyl, tetrahydronaphtyl, anthracenyl or pyrenyl group, are prepared from the corresponding compounds of formula (Ib) according to techniques known to a person skilled in the art.

The invention also relates to 71-conjugated materials of formula (Ib1)

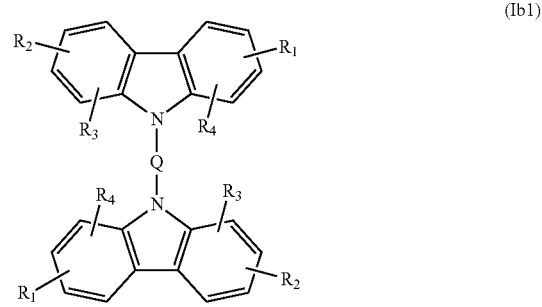
(Ib1)

in which
R$_1$ and R$_2$, identical or different, are respectively in position 3 and 6 or in position 2 and 7 of the carbazole and are selected independently of one another from the group comprising
i. the aryl groups, said aryl groups being able to be substituted by at least one straight or branched C$_1$-C$_5$ alkyl group, in particular a methyl group, ii. the

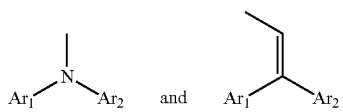

groups in which $Ar_1$ and $Ar_2$, identical or different, each represent independently of one another an aryl group, optionally substituted by one or more substituents, identical or different, selected from:
a. the hydrogen atom,
b. the straight or branched $C_1$-$C_{12}$ alkyl groups, said alkyl groups being able to be saturated or unsaturated and being able to comprise one or more heteroatoms selected from O and S,
c. the straight or branched $C_1$-$C_{12}$ alkoxy groups, said alkoxy groups being able to be saturated or unsaturated and being able to comprise one or more heteroatoms selected from O and S,
d. the oligoethers and
e. the oligothioethers,
provided that $R_1$ and $R_2$ are not simultaneously a hydrogen atom,
$R_3$ and $R_4$, identical or different, occupy the positions left free by $R_1$ and $R_2$ and are selected from:
a. hydrogen,
b. the halogens c. the nitro group,
d. the sulphonate group,
e. the amine groups,
f. the carbonyl groups,
g. the mono- or polycyclic aromatic groups,
h. the straight or branched $C_1$-$C_{12}$ alkyl groups, said alkyl groups being able to be saturated or unsaturated and being able to comprise one or more heteroatoms selected from O and S,
i. the straight or branched $C_1$-$C_{12}$ alkoxy groups, said alkoxy groups being able to be saturated or unsaturated and being able to comprise one or more heteroatoms selected from O and S,
j. the oligoethers and
k. the oligothioethers
and
Q represents a spacer selected from the group comprising:
a. the $C_1$-$C_{12}$ alkylenyl groups,
b. the arylenyl groups,
c. the oligoethers and
d. the oligothioethers.

By "arylenyl groups" is meant a $C_6$-$C_{18}$ arylenyl, substituted or not by one or more $C_1$-$C_{12}$ alkyls. In a particular embodiment of the invention, the arylenyl group represents a fluorenyls group substituted by one or more $C_1$-$C_{12}$ alkyls in position 9 of the fluorenyl.

The following compounds 4 to 11 may be mentioned by way of example of compound (Ib1):

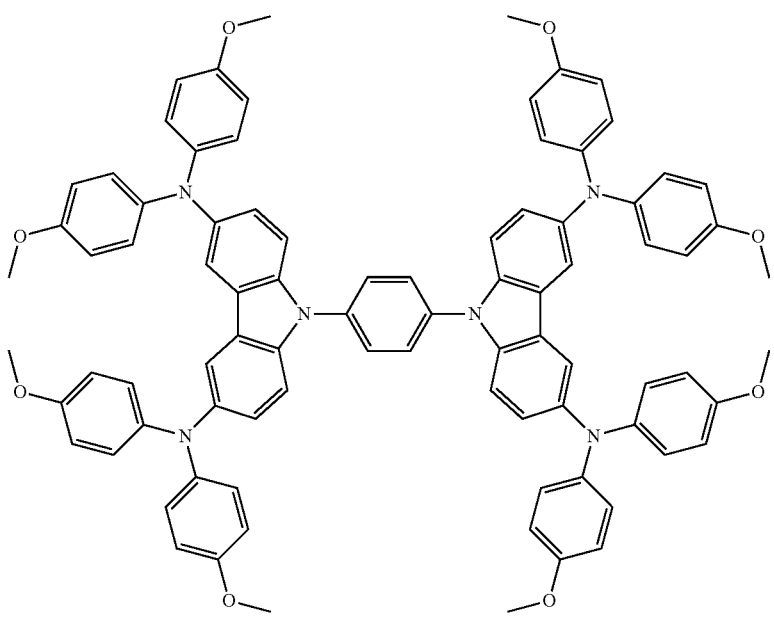

4

-continued
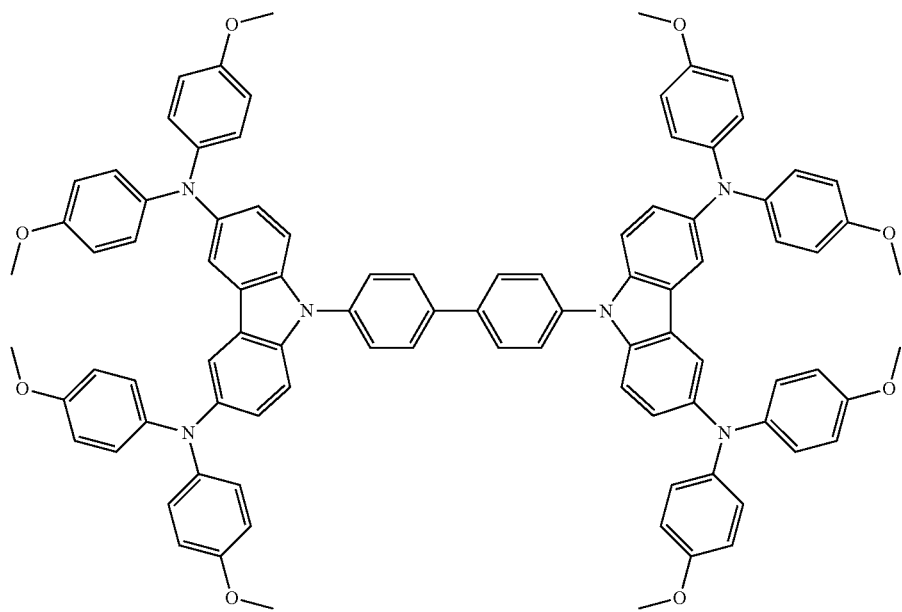
5
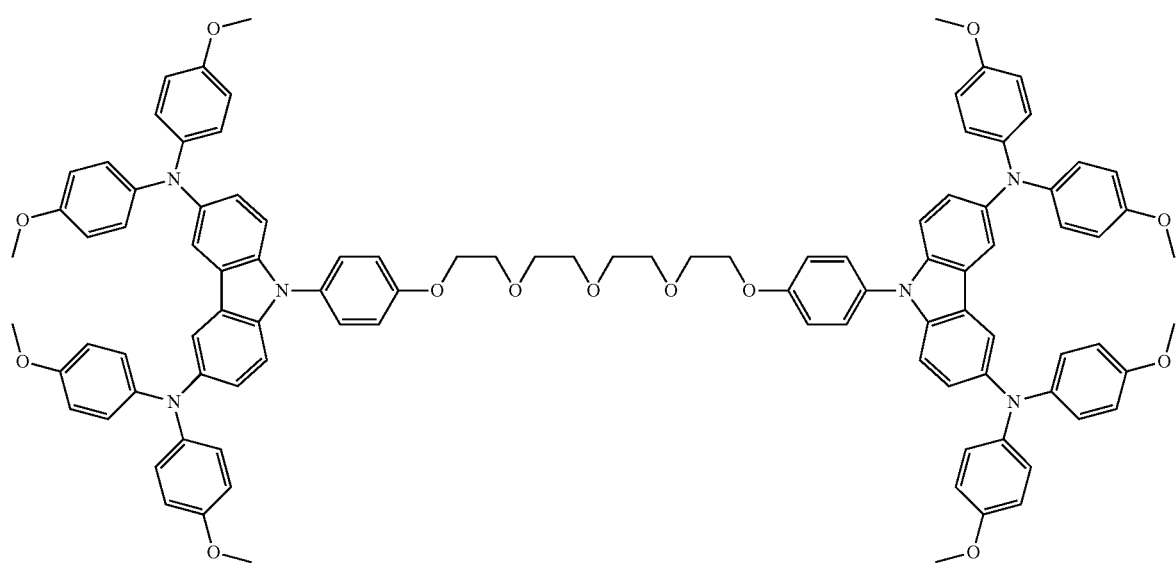
6

7
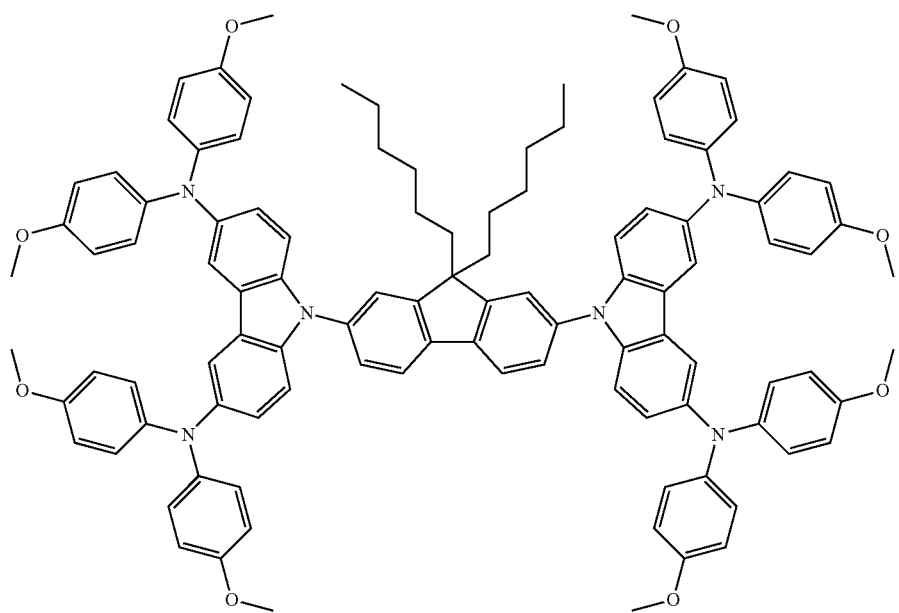
8
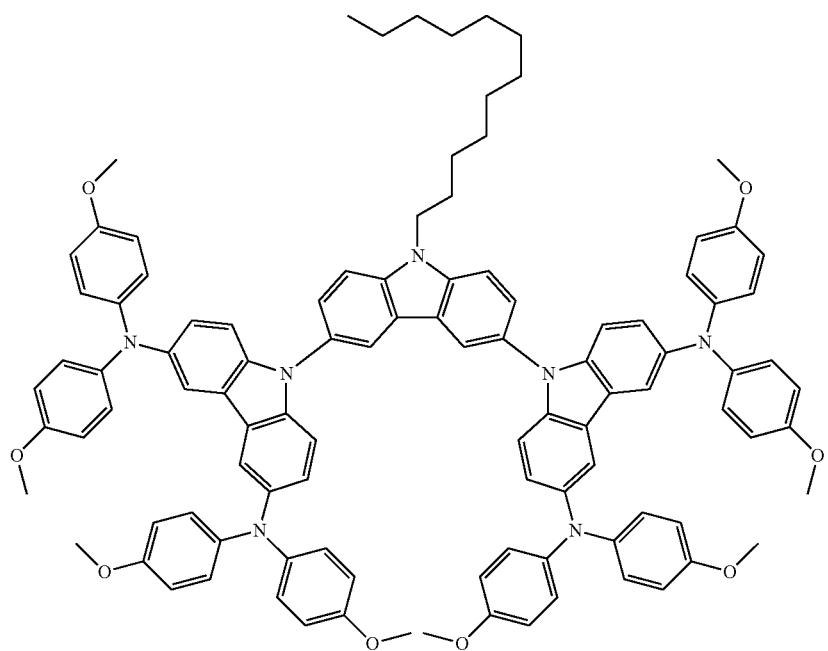

-continued
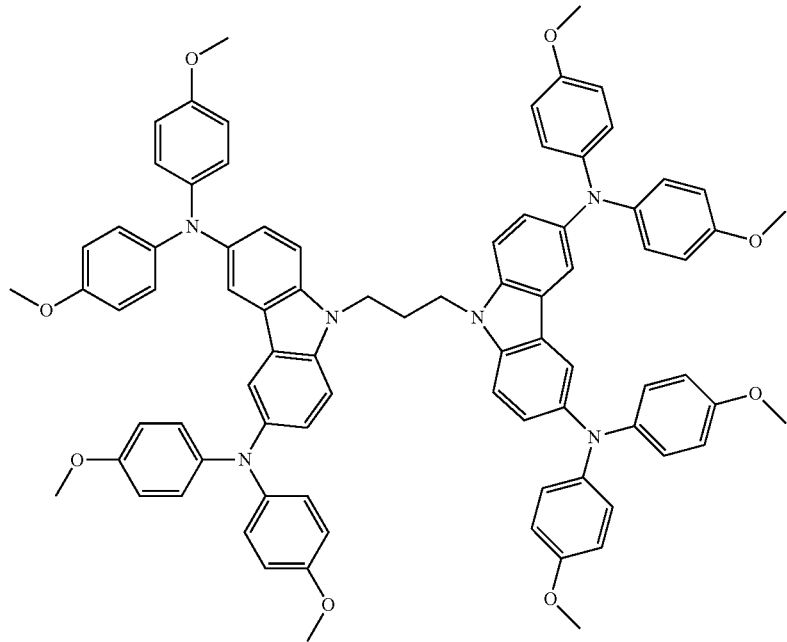
9
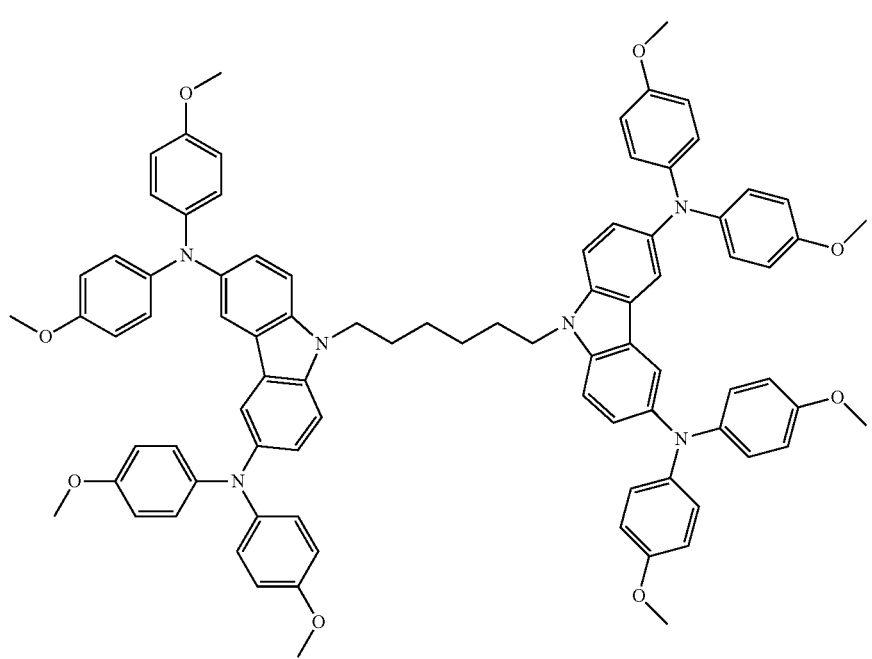
10

11

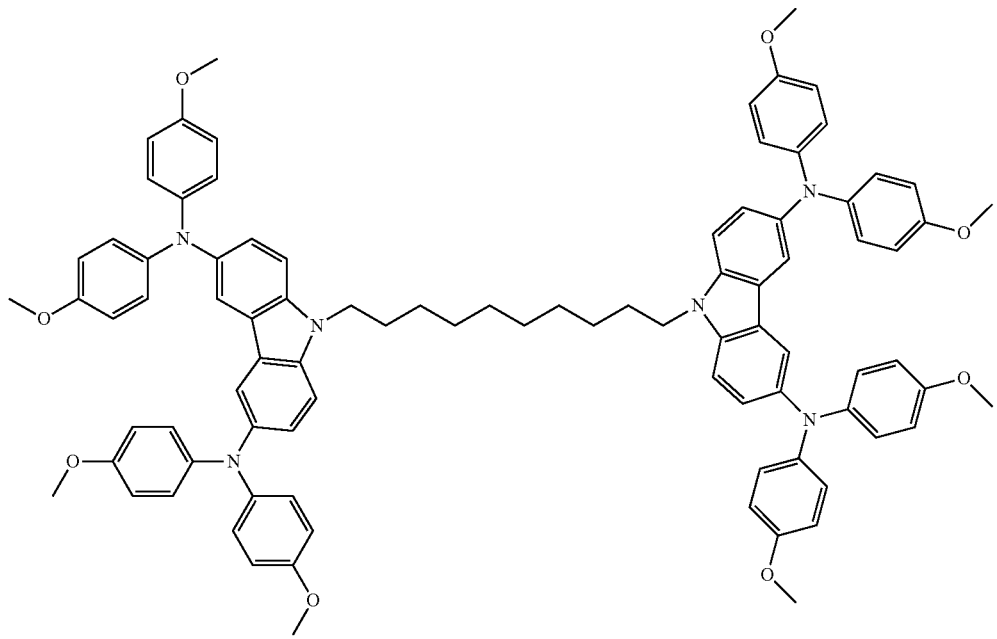

The compounds of formula (Ib1) can be prepared by any technique known to a person skilled in the art, starting from synthons of the invention, by using products that are commercially available or that can be prepared according to techniques known to a person skilled in the art or described in the literature.

Thus it is possible to prepare the compounds of formula (Ib1) by reacting a synthon of formula (I)

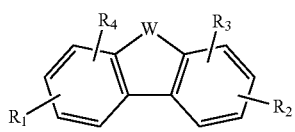

(I)

in which
In which W, $R_1$, $R_2$, $R_3$ and $R_4$ are as previously defined with a compound of formula

X-Q-X in which X represents a halogen atom, in particular an iodine or bromine atom, to obtain a compound of formula (Ib1)

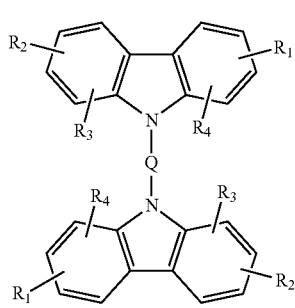

(Ib1)

A very promising application of the present invention is the field of organic photovoltaics and particularly photovoltaic cells with a dye, or dye sensitized solar cells (DSSCs). The process according to the invention has already allowed the synthesis of a certain number of π-conjugated semiconductor organic molecules which have given very promising preliminary results when used instead of liquid electrolyte in DSSCs. The best materials used under the same conditions as the reference molecule on the market (spiro-OMeTAD) give comparable photovoltaic performances. These results demonstrate the great potential of the present invention in this field, since it makes it possible to develop numerous organic semiconductors for the manufacture of solid-state electrolyte DSSCs.

Furthermore, the synthon may also be used to develop dyes having similarities of chemical structure with the semiconductors derived from this same synthon. The fact of having strong affinities between the semiconductor and the dye makes it possible to increase the dye/semiconductor interactions, which promotes the filling of the pores of the sensitized $TiO_2$.

BRIEF DESCRIPTION OF THE DRAWINGS

The following Examples 1 to 11

FIG. 1 shows the current-voltage (J-V) curves in the dark of the devices using the semiconductors comprising the compounds 4 to 7 synthesized according to Examples 2 to 5 in combination with the dye D102 according to Example 11.

FIG. 2: Current-voltage (J-V) curves under illumination of the devices using the semiconductors comprising the compounds 4 to 7 synthesized according to Examples 2 to 5 in combination with the dye D102 according to Example 11.

DETAILED DESCRIPTION

EXAMPLE 1

Figure 1:
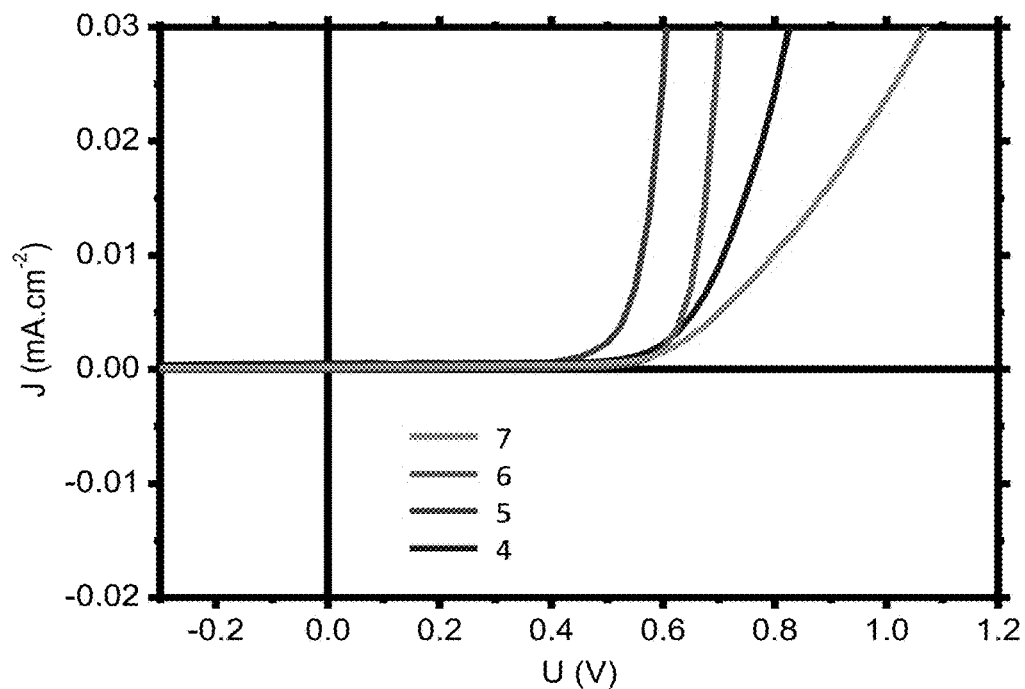
FIGS. 1 and 2 illustrate the invention.

Synthesis of $N^3,N^3,N^6,N^6$,tetrakis(4-methoxyphenyl)-9H-carbazole-3,6-diamine (block 3,6)

It is carried out according to Diagram 1.

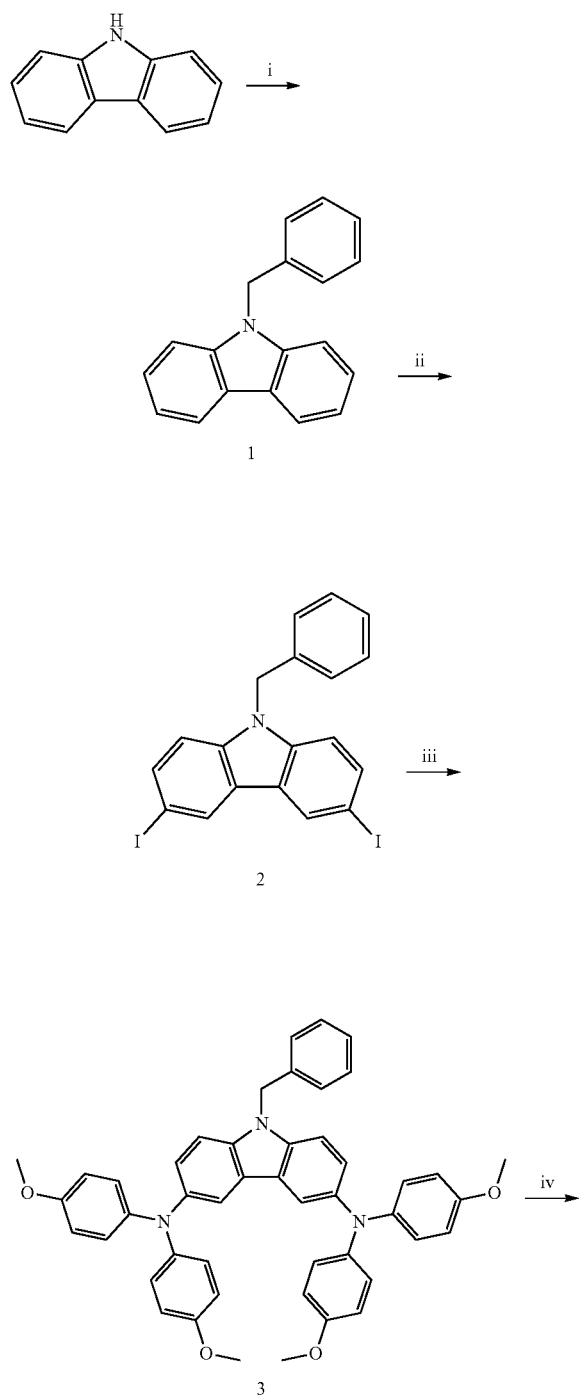

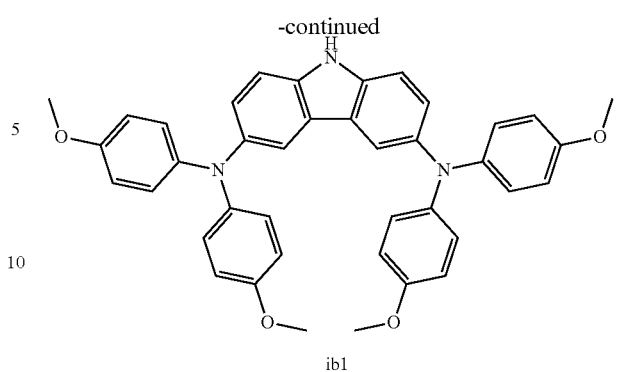

ib1

The first step is protecting the amine in position 9 of the carbazole with a benzyl group according to Estrada, L. A.; Neckers, D. C. *Organic Letters* 2011, 13, 3304. The second step consists of the iodation of positions 3 and 6 of the carbazole nucleus according to Tucker, S. H. *J. Chem. Soc.* 1926, 129, 546. In a third step, a C—N coupling makes it possible to fix the bis(4-methoxyphenyl)amine group at positions 3 and 6 of the carbazole unit according to Yamamoto, T.; Nishiyama, M.; Koie, Y. *Tetrahedron Letters* 1998, 39, 2367. The last step is a deprotection reaction making it possible to remove the benzyl group from position 9 of the carbazole nucleus so as to render the amine function available for subsequent use according to Haddach, A. A.; Kelleman, A.; Deaton-Rewolinski, M. V. *Tetrahedron letters* 2002, 43, 399.

1.1. Synthesis of 9-benzyl-9H-carbazole (1)

Sodium hydride (20 mmol, 0.7 g, 2 eq) is added slowly to a solution of carbazole (10 mmol, 1.7 g, 1 eq) in anhydrous tetrahydrofuran (approximately 30 mL) at ambient temperature. It is noted that a gas is given off (release of $H_2$) and the solution changes colour from yellow to off-white. The mixture is left under stirring at ambient temperature for one hour, when the solution becomes light brown. Benzyl bromide (1.8 mL, 1.5 eq) is added dropwise to the mixture under stirring at ambient temperature.

The mixture is left under stirring for approximately 3 hours and TLCs are carried out to verify if the reaction has finished. At the end of the reaction, water is added to the reaction mixture which is extracted with diethyl ether. The collected organic phases were dried with $MgSO_4$ and the solvent is then evaporated. The solid obtained is washed with n-hexane.

The product is obtained in the form of a white solid that is not very dense.

Yield 80%

1.2. Synthesis of 9-benzyl-3,6-diiodo-9H-carbazole (2)

9-benzyl-9H-carbazole obtained in step 1.1. (16 mmol, 4.1 g, 1 eq) is placed in solution in glacial acetic acid (40-50 mL) in a flask at 80° C. After the 9-benzyl-9H-carbazole has completely dissolved, potassium iodide (KI; 20.8 mmol, 3.5 g, 1.3 eq) and potassium iodate ($KIO_3$; 12.8 mmol, 2.75 g, 0.8 eq) are then added. The temperature is maintained at 80° C. until the $I_2$ formed has been completely consumed. Then the mixture is left under stirring at 80° C. until a white precipitate appears. After the precipitate has appeared, TLCs are carried out to verify if the reaction is complete. A 5% sodium thiosulphate solution is then added to the reaction mixture after returning to ambient temperature and the precipitate is recovered by filtration then washed several times with water. The solid obtained is dried.

The product is obtained in the form of a white solid.
Yield: 98%

1.3. 9-benzyl-$N^3,N^3,N^6,N^6$,tetrakis(4-methoxyphenyl)-9H-carbazole-3,6-diamine (3)

Diphenylamine (10 mmol, 2.3 g, 1 eq), diiodine-containing carbazole obtained in step 1.2. (5 mmol, 2.54 g, 0.5 eq), tri-tert-butylphosphine (0.2 mmol, 0.1 mL, 0.2 eq) and palladium acetate ($Pd(OAc)_2$; 0.2 mmol, 5 mg, 0.2 eq) are added to a Schlenk flask. After adapting the bicol with a condenser, the mixture is placed under an argon atmosphere. Toluene (80 mL) is then added to the mixture of reagents. After stirring for 15 minutes at ambient temperature, sodium terbutoxylate (13 mmol, 1.25 g, 1.3 eq) is added to the reaction mixture. After adding the base, the mixture is taken to reflux at 110° C. for one day. TLCs are carried out to verify the end of the reaction. Once the reaction is complete, the crude is filtered with celite. The filtrate obtained is purified by column chromatography (eluent=petroleum ether/ethyl acetate 8:2).

The product is obtained in the form of a yellow powder.
Yield 93%

1.4. $N^3,N^3,N^6,N^6$,Tetrakis(4-methoxyphenyl)-9H-carbazole-3,6-diamine (Block 3,6)

The benzylcarbazole derivative obtained in step 1.3 (2 mmol, 1.45 g, 1 eq) is added to a flask and the medium is then placed under an argon atmosphere. Dimethyl sulphoxide (DMSO) is then added and the reaction mixture is left under stirring at ambient temperature. A 1 M solution of potassium tert-butylate (KOtBu) in THF (12 mmol, 1.4 g, 6 eq i.e. 12 mL of a 1 M solution of KO-Bu in THF) is then added to the mixture. The argon stream is stopped and dioxygen is bubbled through the reaction medium which remains under stirring at ambient temperature for approximately 3 hours. TLCs are carried out to monitor the progress of the reaction. At the end of the reaction, water is added to the reaction mixture and the crude is extracted with acetate. The organic phase is washed with a saturated solution of $NaHCO_3$ to remove the benzoic acid formed, then with saline solution. The organic phase is then dried with $MgSO_4$ and the solvent is evaporated. After purification by column chromatography (eluent=petroleum ether/ethyl acetate 7:3) the product is obtained in the form of a light yellow powder.
Yield: 80%

EXAMPLE 2

Synthesis of 9,9"-(1,4-phenylene)bis($N^3, N^3,N^6,N^6$, tetrakis(4-methoxyphenyl)-9H-carbazole-3,6-diamine) (Compound 4)

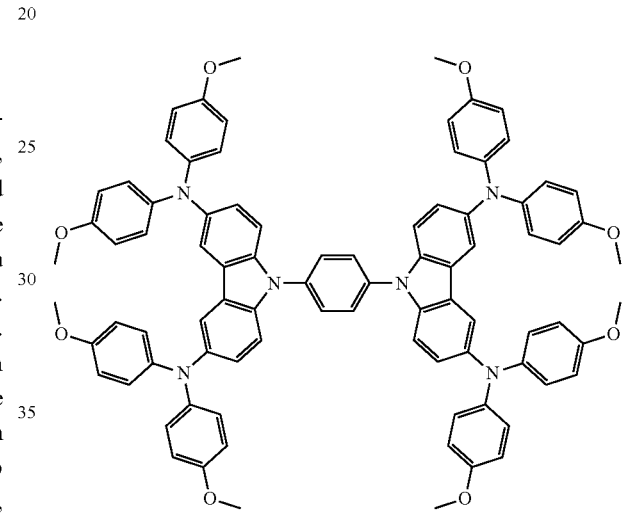

$N^3,N^3,N^6,N^6$,tetrakis(4-methoxyphenyl)-9H-carbazole-3,6-diamine (block 3,6) prepared in Example 1 (0.48 mmol, 300 mg, 1 eq), 4,4' diiodophenyle (0.24 mmol, 81 mg, 0.5 eq), potassium carbonate ($K2CO_3$; 3.84 mmol, 540 mg, 8 eq), copper (1.92 mmol, 120 mg, 4 eq) and 18-crown-6 ether (0.03 mmol, 10 mg, 0.06 eq) are added to a microwave reaction tube. After placing the tube containing the reagents under an inert atmosphere, 3 to 5 ml of ortho-dichlorobenzene is added. The reaction medium is heated by microwave at 210° C. for approximately 1 hour. TLCs were carried out to monitor the progress of the reaction and at the end of the reaction, the reaction mixture is filtered to remove the remaining inorganic reagents. The filtrate obtained is concentrated in an evaporator (by evaporating a part of ortho-dichlorobenzene).

The crude product obtained is purified by precipitation from acetone to obtain a pale green solid.
Yield 50%

EXAMPLE 3

Synthesis of 9,9'-([1,1'°-biphenyl]-4,4'-diyl)bis($N^3$, $N^3,N^6,N^6$, tetrakis(4-methoxyphenyl)-9H-carbazole-3,6-diamine) (Compound 5)

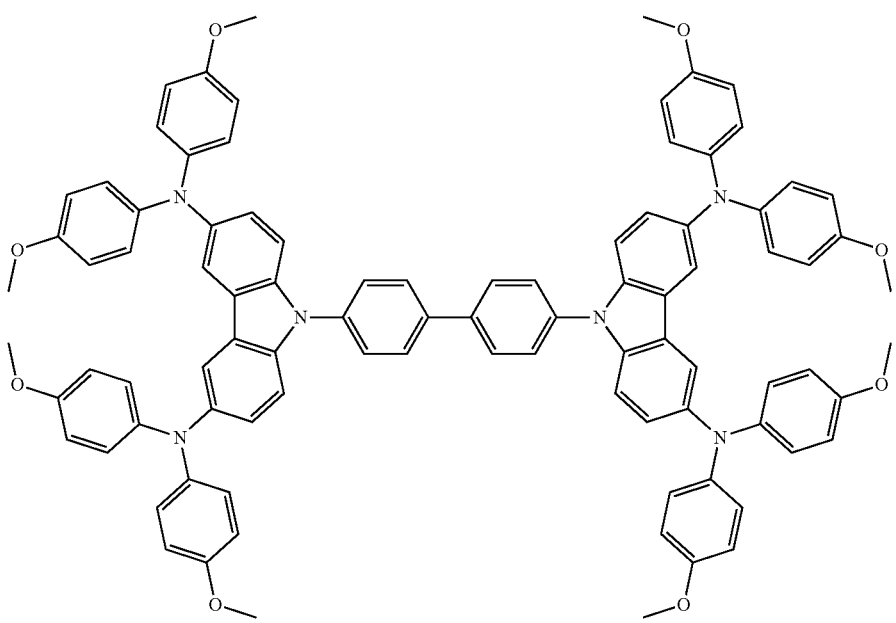

The block [3,6] prepared in Example 1 (0.48 mmol, 300 mg, 1 eq), 4,4'-diiodobiphenyl (0.24 mmol, 98 mg, 0.5 eq), potassium carbonate ($K_2CO_3$; 3.84 mmol, 540 mg, 8 eq), copper (1.92 mmol, 120 mg, 4 eq) and 18-crown-6 ether (0.03 mmol, 10 mg, 0.06 eq) are added to a microwave reaction tube. After placing the tube containing the reagents under an inert atmosphere, 3 to 5 ml of ortho-dichlorobenzene is added. The reaction medium is heated by microwave at 210° C. for approximately 1 hour. TLCs were carried out to monitor the progress of the reaction. At the end of the reaction, the reaction mixture is filtered to remove the remaining inorganic reagents. The filtrate obtained was concentrated in an evaporator (by evaporating a part of ortho-dichlorobenzene). The crude product obtained is purified by precipitation from acetone to obtain a pale green solid.
Yield: 43%

EXAMPLE 4

Synthesis of 9,9'-(9,9-dihexyl-9H-fluorene-2,7-diyl) bis($N^3,N^3,N^6,N^6$, tetrakis(4-methoxyphenyl)-9H-carbazole-3,6-diamine) (Compound 7)

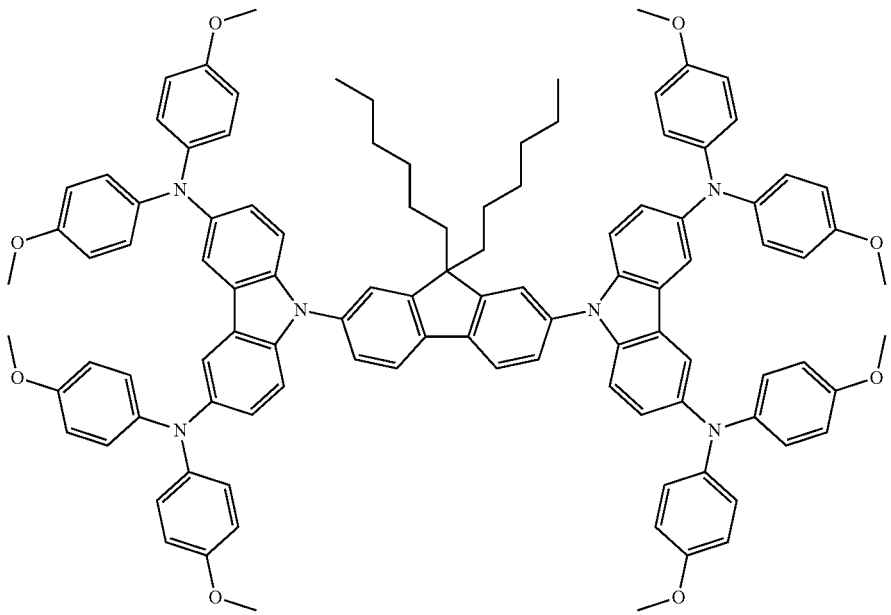

4.1. Synthesis of 9,9'-dihexyl-2,7-diiodo-9H-fluorene

4.1.1. Synthesis of 2,7-diiodo-9H-fluorene

Fluorene (4 g, 24 mmol, 1 eq) is placed in solution in a mixture containing acetic acid (60 mL), water (13 mL) and sulphuric acid (2 mL) at 95° C. After reducing the temperature to 80° C., diiodine (4.2 g, 16.6 mmol, 0.7 eq) and periodic acid (1.85, 8 mmol, 0.33 eq) are then added to the reaction mixture, which is then left under stirring for approximately 1 hour. TLCs were carried out to monitor the progress of the reaction. The precipitate formed was recovered by filtration then washed with a saturated solution of $NaHCO_3$ and water. The crude solid obtained was recrystallized in n-hexane.

The product is obtained in the form of a white solid.
Yield: 50%

4.1.2. Synthesis of 9,9'-dihexyl-2,7-diiodo-9H-1-fluorene

The diiodine-containing fluorene obtained in the preceding step, (4.2 g, 10 mmol, 1 eq), n-bromo-hexane (3.63 g, 22 mmol, 2.2 eq) and potassium tert-butoxide (3.36 g, 30 mmol, 3 eq) are placed in solution in anhydrous THF (30 mL) in a flask. After placing the medium under an inert atmosphere under argon, the reaction mixture is taken to 40° C. then left under stirring overnight. TLCs were carried out to monitor the progress of the reaction. At the end of the reaction, the reaction mixture is allowed to return to ambient temperature, then poured into cold water. The crude product obtained was extracted with diethyl ether, the collected organic phases were washed with saline solution then dried with $MgSO_4$. After evaporation of the solvent, the crude product was purified by column chromatography with the eluent petroleum ether/ethyl acetate (9.5:0.5).

The product is obtained in the form of a white solid.
Yield: 78%

4.2. Synthesis of 9,9'-(9,9-dihexyl-9H-fluorene-2,7-diyl)bis($N^3,N^3,N^6,N^6$, tetrakis(4-methoxyphenyl)-9H-carbazole-3,6-diamine)

The block [3,6] prepared in Example 1 (0.48 mmol, 300 mg, 1 eq), the diiodine-containing fluorene derivative prepared in the preceding step (0.24 mmol, 141 mg, 0.5 eq), potassium carbonate (3.84 mmol, 540 mg, 8 eq), copper (1.92 mmol, 120 mg, 4 eq) and 18-crown-6 ether (0.03 mmol, 10 mg, 0.06 eq) were added to a microwave reaction tube. After placing the tube containing the reagents under an inert atmosphere, 3 to 5 ml of ortho-dichlorobenzene is added. The reaction medium is heated by microwave at 210° C. for 2 hours approximately. TLCs were carried out to monitor the progress of the reaction. At the end of the reaction, the reaction mixture is filtered to remove the remaining the inorganic reagents. The filtrate obtained was concentrated in an evaporator (by evaporating a part of ortho-dichlorobenzene). The crude product obtained is purified by column chromatography using the eluent: petroleum ether/ethyl acetate 7:3.

The product is obtained in the form of a light yellow powder.
Yield: 44%

EXAMPLE 5

Synthesis of 9,9'-(((((oxybis(ethane-2,1-diyl))bis(oxy))bis(ethane-2,1-diyl))bis(4,1-phenylene))bis($N^3,N^3,N^6,N^6$, tetrakis(4-methoxyphenyl)-9H-carbazole-3,6-diamine) (Compound 6)

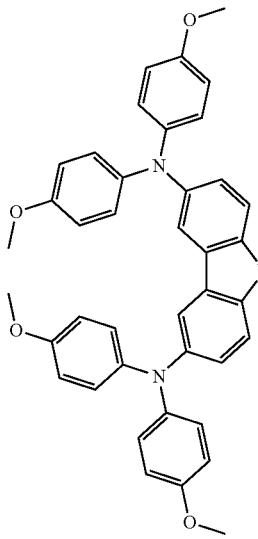
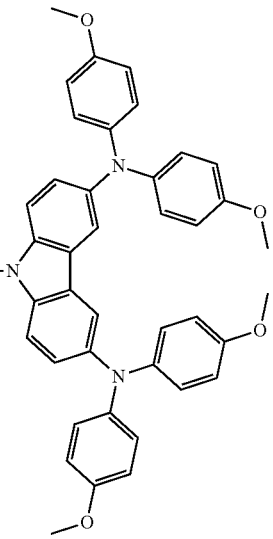

5.1. Synthesis of 4,4'-((((oxybis(ethane-2,1-diyl))bis(oxy))bis(ethane-2,1-diyl))bis(oxy))bis(iodobenzene)

5.1.1. Synthesis of ((oxybis(ethane-2,1-diyl)bis(oxy))bis(ethane-2,1-diyl))bis(4-methythenzenesulphonate) or ethylene glycol ditosylate Glycol ether (10 mmol, 1 eq) is placed in solution in tetrahydrofuran (20 mL) in a flask, tosyl chloride (25 mmol, 2.5 eq) is then added and an aqueous solution of potassium hydroxide (4 ml, 16 M, 64 mmol, 6.4 eq) is then added dropwise to the reaction mixture. After stirring for approximately 7 hours at ambient temperature, TLCs were carried out to monitor the progress of the reaction. At the end of the reaction, the reaction mixture is poured into a solution of cold water and the precipitate formed is recovered by filtration.

The product is obtained in the form of a white solid
Yield: 85%

5.1.2. Synthesis of 4,4'-((((oxybis(ethane-2,1-diyl)bis(oxy))bis(ethane-2,1-diyl))bis(oxy))bis(iodobenzene)

A solution of iodophenol (3.8 g, 17 mmol, 1 eq) is placed in solution in dimethylformamide (60 mL) in a flask, and potassium tert-butylate (2.9 g, 26 mmol, 1.5 eq) is then added slowly. The glycol ether ditosylate derivative obtained in the preceding step (4.3 g, 8.5 mmol, 0.5 eq) is then added to the reaction mixture which is left under stirring overnight at ambient temperature. During the addition of the ditosylate, the formation of a white precipitate is noted. TLCs were carried out to monitor the progress of the reaction. At the end of the reaction, water is added to the reaction mixture. The crude product obtained is then extracted with ethyl acetate and the collected organic phases are washed with a saturated NaHCO₃ solution and dried with MgSO₄.

The product is obtained in the form of a white solid.
Yield: 95%

5.2. Synthesis of 9,9'-(((((oxybis(ethane-2,1-diyl))bis(oxy))bis(ethane-2,1-diyl))bis(4,1-phenylene))bis($N^3,N^3, N^6, N^6$, tetrakis(4-methoxyphenyl)-9H-carbazole-3,6-diamine)

The block [3,6] prepared in Example 1 (0.48 mmol, 300 mg, 1 eq), the diiodine-containing ethylene glycol derivative prepared in the preceding step (0.24 mmol, 98 mg, 0.5 eq), potassium carbonate (3,84 mmol, 540 mg, 8 eq), copper (1.92 mmol, 120 mg, 4 eq) and 18-crown-6 ether (0.03 mmol, 10 mg, 0.06 eq) are added. After placing the tube containing the reagents under an inert atmosphere, 3 to 5 ml of ortho-dichlorobenzene are added. The reaction medium is heated by microwave at 210° C. during 1 hour approximately. TLCs were carried out to monitor the progress of the reaction. At the end of the reaction, the reaction mixture is filtered to remove the remaining the inorganic reagents. The filtrate obtained was concentrated in an evaporator (by evaporating a part of ortho-dichlorobenzene). The crude product obtained is purified by column chromatography using the eluent: petroleum ether/ethyl acetate 7:3.

The product is obtained in the form of a green powder.
Yield: 45%.

EXAMPLE 6

Synthesis of $N^3,N^3,N^6,N^6$,Tetrakis(4-methoxyphenyl)-9-(2-naphthalene)-carbazole-3,6-diamine (compound A), of $N^3,N^3,N^6,N^6$,tetrakis(4-methoxyphenyl)-9-(1-pyrene)-carbazole-3,6-diamine (compound B) and of $N^3,N^3,N^6,N^6$,tetrakis(4-methoxyphenyl)-9-(4-fluorobenzene)-carbazole-3,6-diamine (Compound C)

(Compound A)

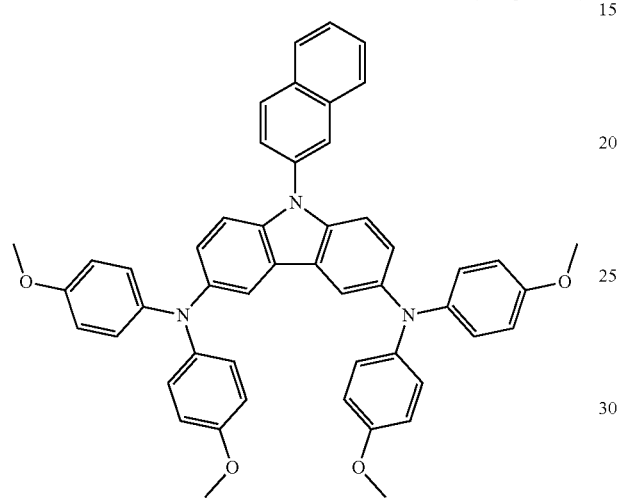

Compound (B)

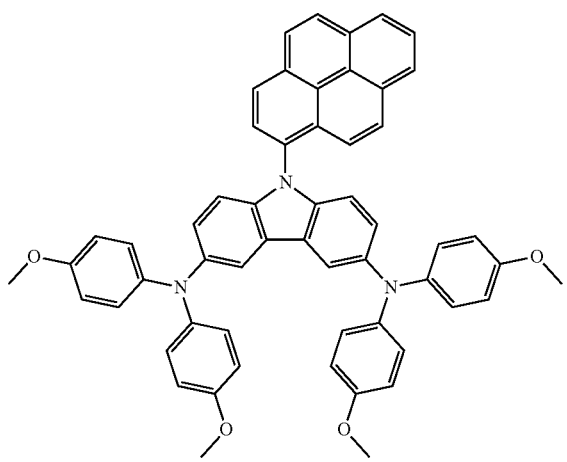

Compound (C)

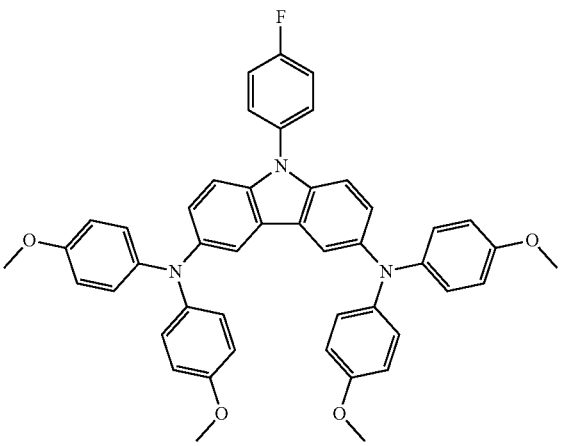

Obtaining Compound A:

The synthon $N^3,N^3,N^6,N^5$,tetrakis(4-methoxyphenyl)-9H-carbazole-3,6-diamine (block 3,6) obtained in Example 1 (1 g, 1 eq), NaOtBu (7 eq), 2-bromonaphthalene (1.1 eq) then Pd(OAc)$_2$ (10%), tri-tert-butylphosphine (20%) as well as toluene (2 ml) are added to a microwave tube under a controlled atmosphere. The solution is heated by microwave at 200° C. for 20 min then, in an oil bath to reflux for 48 hours. The solution is filtered over celite then purified by column chromatography over silica gel. The yield is 87%.

Obtaining Compounds B and C:

Compounds B and C are obtained according to the same protocol, using 1-bromopyrene or 1-fluoro-4-iodobenzene respectively.

The yields obtained for compounds B and C are 83% and 91% respectively.

EXAMPLE 7

Synthesis of 9,9'-(9-dodecanyl-9H-carbazole-3,6-diyl)bis($N^3,N^3,N^6,N^6$, tetrakis(4-methoxyphenyl)-9H-carbazole-3,6-diamine)) (Compound 8)

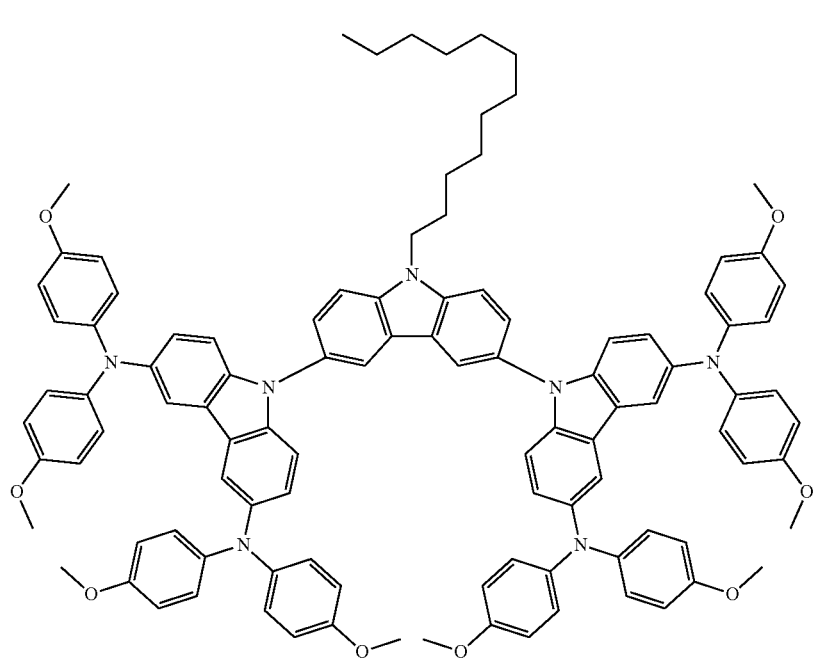

8

The synthon $N^3,N^3,N^6,N^6$,tetrakis(4-methoxyphenyl)-9H-carbazole-3,6-diamine (block 3,6) obtained in Example 1 (1 g, 1 eq), NaOtBu (7 eq), 3,6-dibromo-9-dodecylcarbazole (0.5 eq) then Pd(OAc)$_2$ (10%), tri-tert-butylphosphine (20%) as well as toluene (2 ml) are added to a microwave tube under a controlled atmosphere. The solution is heated by microwave at 200° C. for 20 min, then in an oil bath to reflux for 48 hours. The solution is filtered over celite then purified by column chromatography over silica gel.

The yield is 35%.

EXAMPLE 8

Synthesis of 9,9'-(propyl) bis($N^3,N^3,N^6,N^6$, tetrakis (4-methoxyphenyl)-9H-carbazole-3,6-diamine) (Compound 9)

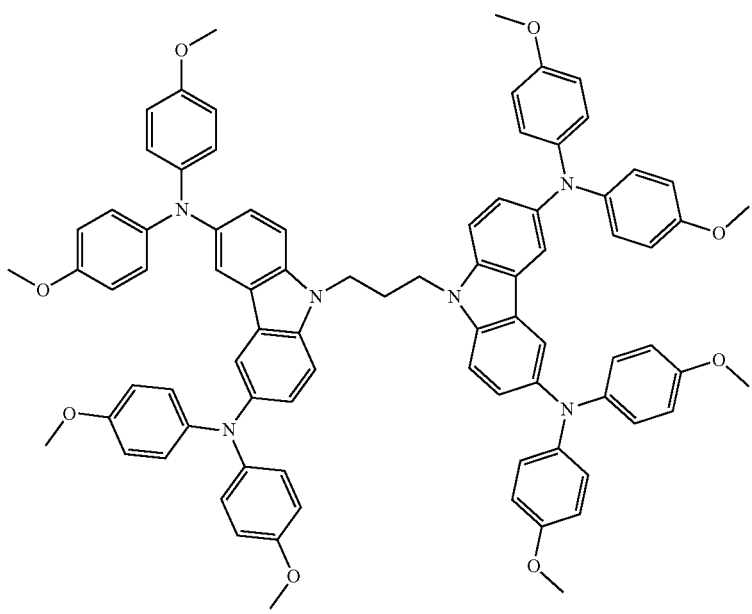

9

The synthon $N^3,N^3,N^6,N^6$,tetrakis(4-methoxyphenyl)-9H-carbazole-3,6-diamine (block 3,6) obtained in Example 1 (1 g, 2.1 eq) and NaH (4 eq) are placed in solution in 10 mL of DMF in a 100 ml Schlenk flask. The mixture is left under stirring at ambient temperature for one hour. 1,3-dibromopropane (1 eq) is added dropwise and the solution is stirred overnight. The reaction is quenched with 5 mL of MeOH. After evaporation of the solvent, the precipitate is solubilized in $CHCl_3$. The organic phase is washed then dried over $MgSO_4$. The reaction crude is purified by column chromatography over silica gel with a solvent mixture: petroleum ether/ethyl acetate. The yield is 35%.

EXAMPLE 9
Synthesis of 9,9'-(hexyl) bis($N^3,N^3,N^6,N^6$, tetrakis(4-methoxyphenyl)-9H-carbazole-3,6-diamine) (Compound 10)
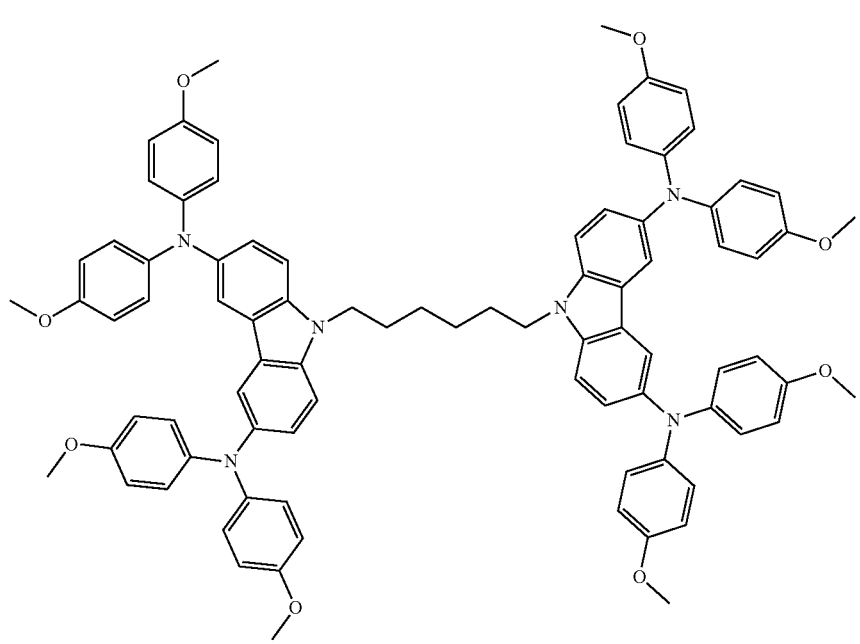
Compound 10 was obtained according to the same protocol as that used in Example 8, using 1,6 dibromohexane respectively.
The yield obtained for the compound is 60%.
EXAMPLE 10
Synthesis of 9,9'-(dodecyl) bis($N^3,N^3,N^6,N^6$, tetrakis(4-methoxyphenyl)-9H-carbazole-3,6-diamine) (Compound 11)
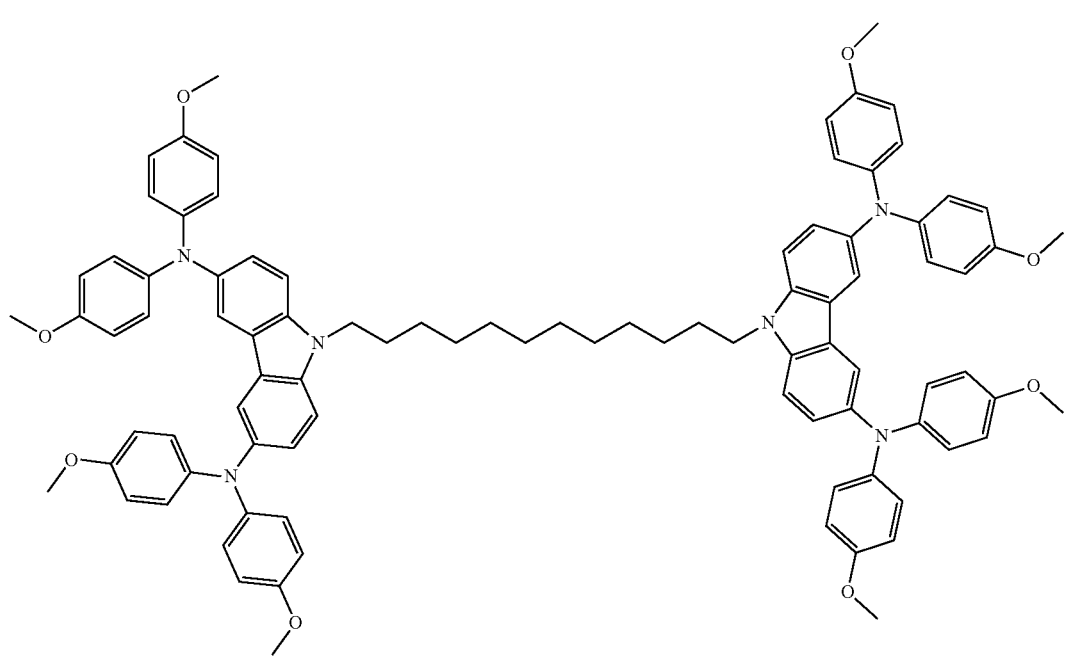

The compound 11 was obtained according to the same protocol as that used in Example 8, using 1,12 dibromododecane respectively.

The yield obtained for the compound is 84%.

EXAMPLE 11

Efficiency of the Molecular Glasses of Examples 2 to 5 as Organic Semiconductors in the ssDSSC Devices The development of dye-sensitized solid-state photovoltaic cells takes place in several steps. It starts with the preparation of the tin oxide-doped fluorine substrate ($SnO_2$:F or FTC) and finishes with the deposition of the gold or silver electrode. The different steps of this manufacturing process will be described successively.

Manufacture of the All-solid-state DSSC Photovoltaic Devices.

The four molecular glasses:
Compound 4: 9,9'-(1,4-phenylene)bis($N^3,N^3,N^6,N^6$,tetrakis(4-methoxyphenyl)-9H-carbazole-3,6-diamine), (obtained according to the process of Example 2);
Compound 5: 9,9'-([1,1'-biphenyl]-4,4'-diyl)bis($N^3,N^3,N^6,N^6$,tetrakis(4-methoxyphenyl)-9H-carbazole-3,6-diamine), (obtained according to the process of Example 3);
Compound 6: 9,9'-(((((oxybis(ethane-2,1-diyl))bis(oxy))bis(ethane-2,1-diyl))bis(4,1-phenylene))bis($N^3,N^3,N^6$,$N^6$,tetrakis(4-methoxyphenyl)-9H-carbazole-3,6-diamine), (obtained according to the process of Example 5);
Compound 7: 9,9'-(9,9-dihexyl-9H-fluorene-2,7-diyl)bis($N^3,N^3,N^6,N^6$, tetrakis(4-methoxyphenyl)-9H-carbazole-3,6-diamine), (obtained according to the process of Example 4), were used as organic semiconductors for the DSSC devices in combination with the dye D102 which is a commercial product, the chemical structure of which is presented below.

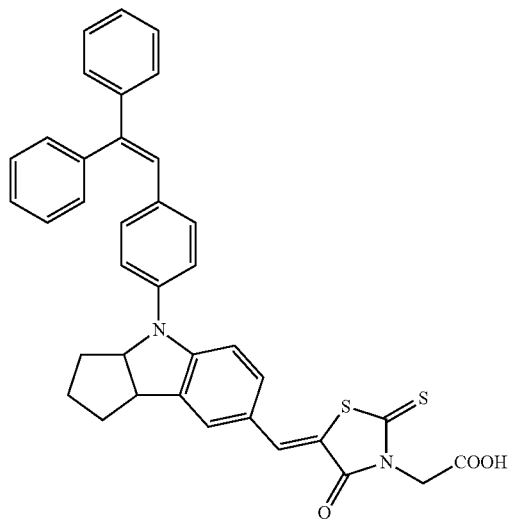

D102

Figure 2:
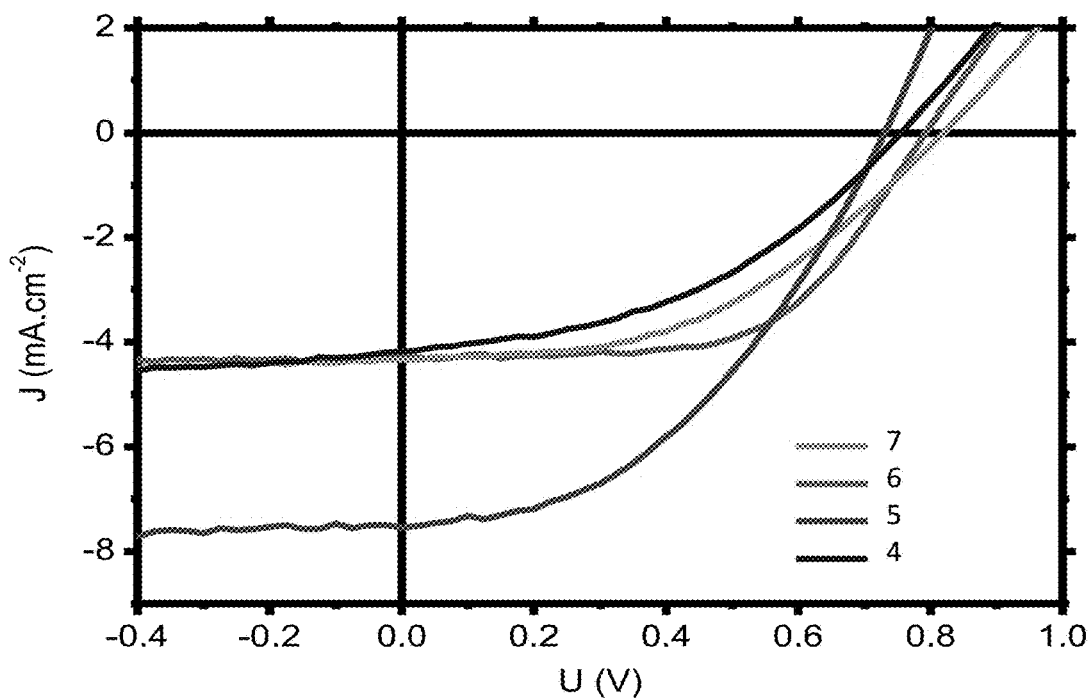

The manufacture of all-solid-state DSSC photovoltaic devices (ssDSSC) was carried out according to the protocol well known to a person skilled in the art and in particular described in the publication by Puckyte et al ("Carbazole-based molecular glasses for efficient solid-state dye-sensitized solar cells", Journal of Power Sources, 2013, vol 233, p86-92). The measurements of the performances of the devices are carried out in the dark and under illumination (AM 1.5 G). The composition of the cell is as follows: FTO/$TiO_2$/D102/HTM/Ag. The semiconductors are represented by the hole transporting materials (HTMs). The solutions used for the development of the hole transporting layer have a HTM concentration of 200 mg/mL in chlorobenzene, in the presence of additives commonly used for DSSCs, namely lithium bis(trifluoromethane)sulphonimide (LiTFSI) and 4-tertbutylpyridine. The results obtained are presented in FIGS. 1 and 2 and summarized in Table 1 below.

TABLE 1

Photovoltaic parameters of the devices using HTMs comprising compounds 4, 5, 6 and 7 in combination with the dye D102 (in the dark and under illumination)

| Glasses | $J_{SC}$ (mA · cm−2) | $V_{OC}$ (V) | FF (%) | Yield (%) |
|---|---|---|---|---|
| Compound 4 | 4.17 | 0.75 | 43 | 1.34 |
| Compound 5 | 7.45 | 0.73 | 43 | 2.36 |
| Compound 6 | 4.31 | 0.79 | 59 | 2.03 |
| Compound 7 | 4.33 | 0.82 | 46 | 1.63 |

Definitions of the abbreviations used in Table 1:
Jsc: short-circuit current density (mA · cm−2)
Voc: open-circuit voltage (V)
FF: form factor (%)

CONCLUSION

The characteristics were obtained in the dark and under illumination (AM 1.5 G). The four devices show a diode characteristic in the dark and a photovoltaic effect under illumination via the appearance of a photogenerated current (see FIGS. 1 et 2). The short-circuit current densities obtained are situated between 4.17 mA·cm$^{-2}$ and 7.45 mA·cm$^{-2}$ and the open-circuit voltage values are comprised between 0.73 V and 0.82 V. The photovoltaic conversion efficiencies range from 1.34% to 2.36%. Compound 5 is the one which allowed the best conversion efficiency to be obtained, which is 2.36%.

The invention claimed is:

1. A process for the synthesis of π-conjugated materials of formula (1b)

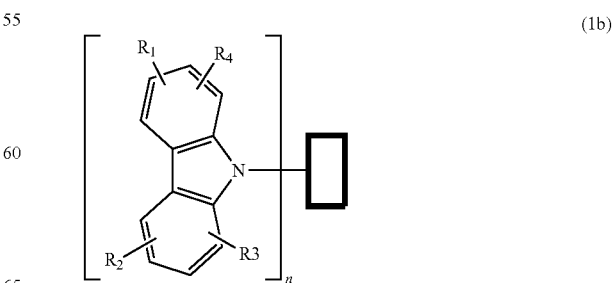

(1b)

in which

represents a central polyfunctional unit bearing functions allowing grafting in position 9 of the carbazole nucleus, n is an integer equal to or greater than 2, advantageously comprised between 2 and 5, $R_1$ and $R_2$, identical or different, are respectively in position 3 and 6 or in position 2 and 7 of the ring and are selected independently of one another from the group comprising:
i. hydrogen;
ii. aryl groups, said aryl groups being able to be substituted by at least one straight or branched $C_1$-$C_5$ alkyl group;
iii.

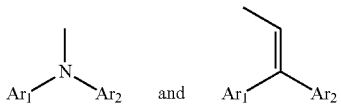

groups in which $Ar_1$ and $Ar_2$, identical or different, each represent independently of one another an aryl group, optionally substituted by one or more substituents, identical or different, selected from:
a. a hydrogen atom;
b. straight or branched $C_1$-$C_{12}$ alkyl groups, said alkyl groups being able to be saturated or unsaturated and being able to comprise one or more heteroatoms selected from O and S;
c. straight or branched $C_1$-$C_{12}$ alkoxy groups, said alkoxy groups being able to be saturated or unsaturated and being able to comprise one or more heteroatoms selected from O and S;
d. oligoethers; and
e. oligothioethers, provided that $R_1$ and $R_2$ are not simultaneously a hydrogen atom, $R_3$ and $R_4$, identical or different, occupy the positions left free by $R_1$ and $R_2$ and are selected from:
a. hydrogen;
b. halogens;
c. nitro group;
d. sulphonate group;
e. amine groups;
f. carbonyl groups;
g. mono- or polycyclic aromatic groups;
h. straight or branched $C_1$-$C_{12}$ alkyl groups, said alkyl groups being able to be saturated or unsaturated and being able to comprise one or more heteroatoms selected from O and S;
i. straight or branched $C_1$-$C_{12}$ alkoxy groups, said alkoxy groups being able to be saturated or unsaturated and being able to comprise one or more heteroatoms selected from O and S;
j. oligoethers; and
k. oligothioethers, the process comprising a step of reacting a synthon of formula (I)

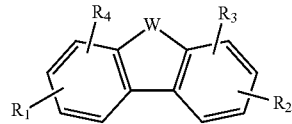

in which
W represents an —N(H)— group,
$R_1$ and $R_2$, identical or different, are respectively in position 3 and 6 or in position 2 and 7 of the ring and are selected independently of one another from the group comprising:
i. hydrogen;
ii. the mono- or polycyclic aromatic groups, said groups being able to be substituted by at least one straight or branched $C_1$-$C_{12}$ alkyl group, in particular a methyl group, or by a straight or branched $C_1$-$C_{12}$ alkoxy group, in particular a methoxy;
iii.

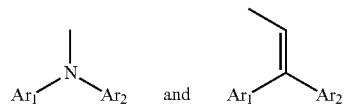

groups in which $Ar_1$ and $Ar_2$, identical or different, each represent independently of one another an aryl group, optionally substituted by one or more substituents, identical or different, selected from:
a. hydrogen atom;
b. straight or branched $C_1$-$C_{12}$ alkyl groups, said alkyl groups being able to be saturated or unsaturated and being able to comprise one or more heteroatoms selected from O and S;
c. straight or branched $C_1$-$C_{12}$ alkoxy groups, said alkoxy groups being able to be saturated or unsaturated and being able to comprise one or more heteroatoms selected from O and S,
d. oligoethers; and
e. oligothioethers, provided that $R_1$ and $R_2$ are not simultaneously a hydrogen atom, $R_3$ and $R_4$, identical or different, occupy the positions left free by $R_1$ and $R_2$ and are selected from:
a. hydrogen;
b. halogens;
c. a nitro group;
d. a sulphonate group;
e. amine groups;
f. carbonyl groups;
g. mono- or polycyclic aromatic groups;
h. straight or branched $C_1$-$C_{12}$ alkyl groups, said alkyl groups being able to be saturated or unsaturated and being able to comprise one or more heteroatoms selected from O and S;
i. straight or branched $C_1$-$C_{12}$ alkoxy groups, said alkoxy groups being able to be saturated or unsaturated and being able to comprise one or more heteroatoms selected from O and S; and
j. oligoethers;

with a compound of formula X-Q-X, in which X represents a halogen atom and Q represents a spacer selected from a group consisting of: $C_1$-$C_{12}$ alkylenyl groups, arylenyl groups, oligoethers and oligothioethers.

2. The process according to claim 1, characterized in that in the compound of formula (I), $R_1$ and $R_2$ each represent, independently of one another, a group selected from:
   i. the phenyl, naphthyl, anthracenyl, indenyl, biphenyl, terphenyl, carbazolyl groups, said groups being able to be substituted by at least one straight or branched $C_1$-$C_{12}$ alkyl group, in particular a methyl group;
   ii.

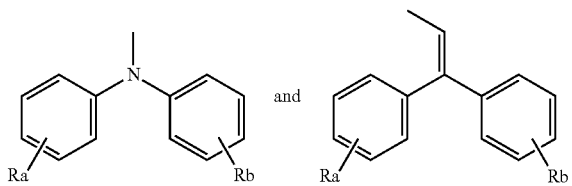

groups in which Ra and Rb, identical or different, each represent, independently of one another:
   a. either a hydrogen atom;
   b. or a straight or branched $C_1$-$C_{12}$ alkyl group, said alkyl group being able to be saturated or unsaturated and being able to comprise one or more heteroatoms selected from O and S;
   c. or a straight or branched $C_1$-$C_{12}$ alkoxy group, said alkoxy group being able to be saturated or unsaturated and being able to comprise one or more heteroatoms selected from O and S;
   d. or an oligoether;
   e. or an oligothioether.

3. The process according to claim 1, characterized in that in the compound of formula (I), $R_3$ and $R_4$ each represent a hydrogen atom.

4. The process for the synthesis of π-conjugated materials according to claim 1, further comprising:
   a) a step of protecting W when W represents an —N(H)— group in the compound of formula (II)

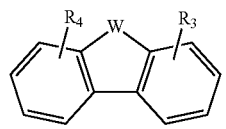

(II)

and
   $R_3$ and $R_4$, identical or different, are selected from:
   i. hydrogen;
   ii. halogens;
   iii. a nitro group;
   iv. a sulphonate group;
   v. amine groups;
   vi. carbonyl groups;
   vii. mono- or polycyclic aromatic groups;
   viii. straight or branched $C_1$-$C_{12}$ alkyl groups, said alkyl groups being able to be saturated or unsaturated and being able to comprise one or more heteroatoms selected from O and S;
   ix. straight or branched $C_1$-$C_{12}$ alkoxy groups, said alkoxy groups being able to be saturated or unsaturated and being able to comprise one or more heteroatoms selected from O and S;
   x. oligoethers; and
   xi. oligothioethers, provided that if $R_3$ is in position 2 then $R_4$ is not in position 7 and if $R_3$ is in position 3 then $R_4$ is not in position 6, to give a compound of formula (III)

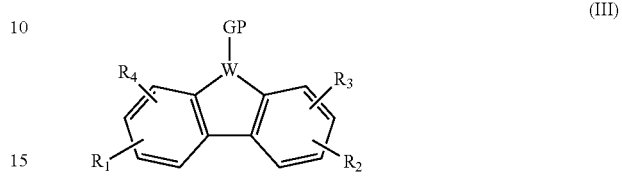

(III)

in which GP is an amine protecting group,
   b) treating the compound of formula (III) with a halogenated derivative, to give a compound of formula (IVb)

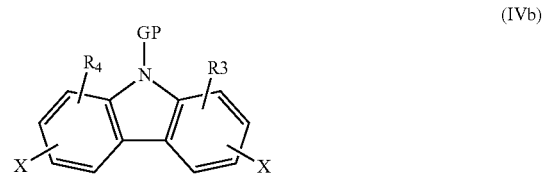

(IVb)

in which
   $R_3$ and $R_4$ are as defined in claim 1 and
   X, in position 3 and 6 of the carbazole represents a halogen atom, in particular an iodine or bromine atom, c) a coupling reaction of said compound of formula (IVb) to give a compound of formula (Vb)

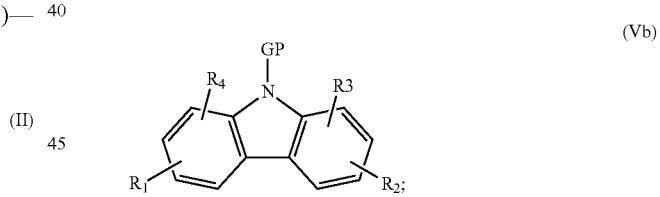

(Vb)

in which $R_1$, $R_2$, $R_3$ and $R_4$ are as defined in claim 1.

5. A process for the synthesis of π-conjugated materials of formula (Ib')

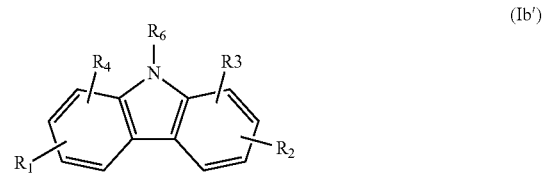

(Ib')

in which
   $R_1$ and $R_2$, identical or different, are respectively in position 3 and 6 or in position 2 and 7 of the ring and are selected independently of one another from the group comprising:

i. hydrogen;
ii. the aryl groups, said aryl groups being able to be substituted by at least one straight or branched $C_1$-$C_{12}$ alkyl group, in particular a methyl group;
iii.

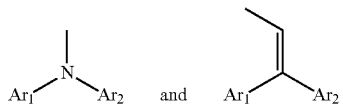

groups in which $A_1$ and $A_2$, identical or different, each represent independently of one another an aryl group, optionally substituted by one or more substituents, identical or different, selected from:
a. hydrogen atom;
b. straight or branched $C_1$-$C_{12}$ alkyl groups, said alkyl groups being able to be saturated or unsaturated and being able to comprise one or more heteroatoms selected from O and S;
c. straight or branched $C_1$-$C_{12}$ alkoxy groups, said alkoxy groups being able to be saturated or unsaturated and being able to comprise one or more heteroatoms selected from O and S;
d. oligoethers; and
e. oligothioethers,
provided that $R_1$ and $R_2$ are not simultaneously a hydrogen atom,
$R_3$ and $R_4$, identical or different, occupy the positions left free by $R_1$ and $R_2$ and are selected from:
a. hydrogen;
b. halogens;
c. a nitro group;
d. a sulphonate group;
e. an amine group;
f. a carbonyl group;
g. mono- or polycyclic aromatic groups;
h. straight or branched $C_1$-$C_{12}$ alkyl groups, said alkyl groups being able to be saturated or unsaturated and being able to comprise one or more heteroatoms selected from O and S;
i. straight or branched $C_1$-$C_{12}$ alkoxy groups, said alkoxy groups being able to be saturated or unsaturated and being able to comprise one or more heteroatoms selected from O and S;
f. oligoethers; and
g. oligothioethers;
and
$R_6$ represents either a straight or branched $C_1$-$C_{12}$ alkyl group, or a $C_6$-$C_{18}$ aryl group, in particular a benzene or methoxybenzene (anisole) group, or an amine protecting group, in particular a benzyl group, optionally substituted by a $C_1$-$C_5$ alkoxy group, or a $C_6$-$C_{18}$ aryl group substituted by a halogen, in particular fluorine or substituted by a straight or branched fluorinated $C_1$-$C_{12}$ alkyl group, in particular trifluoromethyl ($CF_3$), or a bi-, tri or tetracyclic group comprising from 10 to 18 carbon atoms, such as for example a naphthyl, tetrahydronaphthyl, anthracenyl or pyrenyl group,
the process comprising a step of reacting a synthon of formula (I)

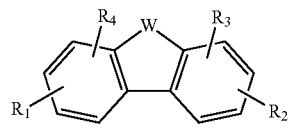

in which
W represents an —N(H)— group,
$R_1$ and $R_2$, identical or different, are respectively in position 3 and 6 or in position 2 and 7 of the ring and are selected independently of one another from the group comprising:
i. hydrogen;
ii. the mono- or polycyclic aromatic groups, said groups being able to be substituted by at least one straight or branched $C_1$-$C_{12}$ alkyl group, in particular a methyl group, or by a straight or branched $C_1$-$C_{12}$ alkoxy group, in particular a methoxy;
iii.

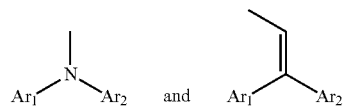

groups in which $A_1$ and $A_2$, identical or different, each represent independently of one another an aryl group, optionally substituted by one or more substituents, identical or different, selected from:
f. hydrogen atom;
g. straight or branched $C_1$-$C_{12}$ alkyl groups, said alkyl groups being able to be saturated or unsaturated and being able to comprise one or more heteroatoms selected from O and S;
h. straight or branched $C_1$-$C_{12}$ alkoxy groups, said alkoxy groups being able to be saturated or unsaturated and being able to comprise one or more heteroatoms selected from O and S,
i. oligoethers; and
j. oligothioethers,
provided that $R_1$ and $R_2$ are not simultaneously a hydrogen atom,
$R_3$ and $R_4$, identical or different, occupy the positions left free by $R_1$ and $R_2$ and are selected from:
k. hydrogen;
l. halogens;
m. a nitro group;
n. a sulphonate group;
o. amine groups;
p. carbonyl groups;
q. mono- or polycyclic aromatic groups;
r. straight or branched $C_1$-$C_{12}$ alkyl groups, said alkyl groups being able to be saturated or unsaturated and being able to comprise one or more heteroatoms selected from O and S;
s. straight or branched $C_1$-$C_{12}$ alkoxy groups, said alkoxy groups being able to be saturated or unsaturated and being able to comprise one or more heteroatoms selected from O and S; and
t. oligoethers;
with a compound of formula X-Q-X, in which X represents a halogen atom and Q represents a spacer selected from a group consisting of: $C_1$-$C_{12}$ alkylenyl groups, arylenyl groups, oligoethers and oligothioethers.

6. The process according to claim 5, characterized in that in the compound of formula (I), R1 and R2 each represent, independently of one another, a group selected from:
  i. the phenyl, naphthyl, anthracenyl, indenyl, biphenyl, terphenyl, carbazolyl groups, said groups being able to be substituted by at least one straight or branched $C_1$-$C_{12}$ alkyl group, in particular a methyl group;
  ii.

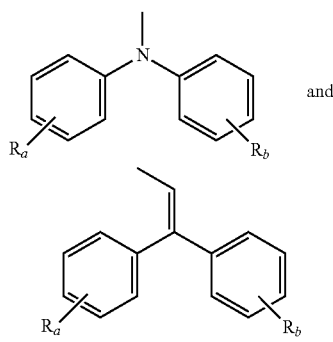

and groups in which Ra and Rb, identical or different, each represent, independently of one another:
  a. either a hydrogen atom;
  b. or a straight or branched $C_1$-$C_{12}$ alkyl group, said alkyl group being able to be saturated or unsaturated and being able to comprise one or more heteroatoms selected from O and S;
  c. or a straight or branched $C_1$-$C_{12}$ alkoxy group, said alkoxy group being able to be saturated or unsaturated and being able to comprise one or more heteroatoms selected from O and S;
  d. or an oligoether;
  e. or an oligothioether.

7. The process according to claim 5, characterized in that in the compound of formula (I), R3 and R4 each represent a hydrogen atom.

8. The process for the synthesis of π-conjugated materials according to claim 5 further comprising:
  a) a step of protecting W when W represents an —N(H)— group in the compound of formula (II)

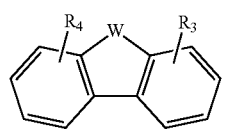

(II)

and
$R_3$ and $R_4$, identical or different, are selected from:
xii. hydrogen;
xiii. halogens;
xiv. a nitro group;
xv. a sulphonate group;
xvi. amine groups;
xvii. carbonyl groups;
xviii. mono- or polycyclic aromatic groups;
xix. straight or branched $C_1$-$C_{12}$ alkyl groups, said alkyl groups being able to be saturated or unsaturated and being able to comprise one or more heteroatoms selected from O and S;
xx. straight or branched $C_1$-$C_{12}$ alkoxy groups, said alkoxy groups being able to be saturated or unsaturated and being able to comprise one or more heteroatoms selected from O and S;
xxi. oligoethers; and
xxii. oligothioethers,
provided that if $R_3$ is in position 2 then $R_4$ is not in position 7 and if $R_3$ is in position 3 then $R_4$ is not in position 6,
to give a compound of formula (III)

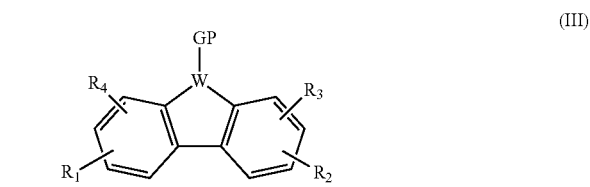

(III)

in which GP is an amine protecting group,
b) treating the compound of formula (III) with a halogenated derivative, to give a compound of formula (IVb)

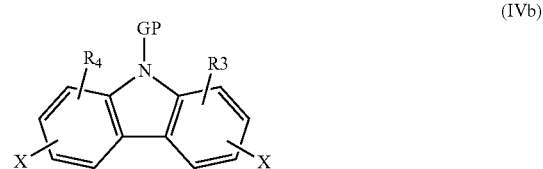

(IVb)

in which
$R_3$ and $R_4$ are as defined in claim 1 and
X, in position 3 and 6 of the carbazole represents a halogen atom, in particular an iodine or bromine atom,
c) a coupling reaction of said compound of formula (IVb) to give a compound of formula (Vb)

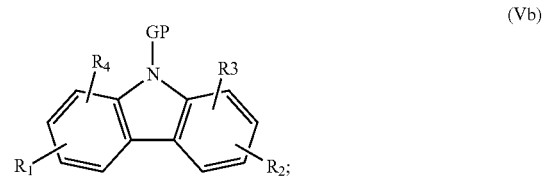

(Vb)

in which $R_1$, $R_2$, $R_3$ and $R_4$ are as defined in claim 5.

* * * * *